United States Patent [19]

Daluge

[11] Patent Number: 5,049,671
[45] Date of Patent: Sep. 17, 1991

[54] 6-SUBSTITUTED PURINE CARBOCYCLIC NUCLEOSIDES

[75] Inventor: Susan M. Daluge, Chapel Hill, N.C.
[73] Assignee: Burroughs Wellcome Co., Research Triangle Park, N.C.
[21] Appl. No.: 455,538
[22] Filed: Dec. 22, 1989

Related U.S. Application Data

[63] Continuation-in-part of Ser. No. 371,789, Jun. 27, 1989, abandoned.

[30] Foreign Application Priority Data

Jun. 27, 1988 [GB] United Kingdom .............. 8815265.7

[51] Int. Cl.$^5$ .................. C07D 473/16; C07D 473/18; C07D 473/24
[52] U.S. Cl. ..................................... 544/276; 544/277; 544/118; 544/324; 544/325
[58] Field of Search ...................... 544/276, 277, 244; 514/261, 262, 265, 266, 81

[56] References Cited

U.S. PATENT DOCUMENTS

| | | | |
|---|---|---|---|
| 4,543,255 | 9/1985 | Shealy et al. | 514/258 |
| 4,605,659 | 8/1986 | Verheyden et al. | 514/262 |
| 4,613,666 | 9/1986 | Fukukawa et al. | 544/277 |
| 4,859,677 | 8/1989 | Borchardt et al. | 544/261 |
| 4,916,224 | 4/1990 | Vince et al. | 544/254 |
| 4,931,559 | 6/1990 | Vince et al. | 544/276 |

FOREIGN PATENT DOCUMENTS

| | | |
|---|---|---|
| 28871/89 | 7/1989 | Australia . |
| 2867189 | 7/1989 | Australia . |
| 0236935 | 9/1987 | European Pat. Off. . |
| 0325460 | 7/1989 | European Pat. Off. . |
| 0346132A1 | 12/1989 | European Pat. Off. . |
| 6422853 | 1/1989 | Japan . |
| 2179349A | 3/1987 | United Kingdom . |
| 2217320 A | 10/1989 | United Kingdom . |

OTHER PUBLICATIONS

Marquez, et al., Medicinal Research Reviews, vol. 6, No. 1, pp. 1–3, 8–10, 21, 25 and 37–40 (1986).
Trost, et al., J. Am. Chem. Soc., vol. 110, No. 2, pp. 621–622 (01/20/88).
Synthesis of Cargocyclic Aminonucleosides, S. Daluge & R. Vince, J. Org. Chem., vol. 43, No. 12, 1978, pp. 2311–2320.
Antiviral Research Program and Abstracts of the Second International Conference on Antiviral Research, Williamsburg W. VA, U.S.A., 10–14, Apr. 1988, vol. 9, No. 1/2, p. 120, abstract entitled "Patent and Selective Antiviral Activity of a New Nucleoside Analog".
White, et al., Biochem. Biophysical Research Communications, vol. 161, No. 2, pp. 393–398, Jun. 15, 1989, Comparison of the Effect of Carbovir, AZT and etc.
Yeom, et al., Antimicrobial Agents and Chemotherapy, Feb. 1989, pp. 171–175, vol. 33, No. 2, Pharmacokinetics and Bioavailability of Carbovir, a Carbocyclic Nucleoside Active against Human Immunodeficiency Virus, in Rats.
Marquez, et al., Nucleosides & Nucleotides, 6(1&2), 239–244, (1987), Synthesis of 2',3'-Dideoxycyclopentenyl Carbocyclic Nucleosides as Potential Drugs for the Treatment of Aids.
Vince, et al., Bio. Chem. & Bio. Phys. Res. Comm., pp. 1046–1053, vol. 156, No. 2, 1988, Potent and Selective Activity of a New Carbocyclic Nucleoside Analog (Carbovir:NSC 614846) Against Human Immunod. Virus in Vitro.
Rory P. Remmel, Journal of Chromatography, 489, (1989), pp. 323–331, Liquid Chromatographic Assay of Carbovir, A Carbocyclic Nucleoside Active Against Human Immunodeficiency Virus.
Koppel, et al., Potential Purine Antagonists, XIII, Oct. 1958, pp. 1457–1460, Potential Purine Antagonists, XIII, Synthesis of Some 8-Methylpurines[1].
Madhaven, et al., J. Org. Chem., 1986, 51, pp. 1287–1293, A Novel and Stereospecific Synthesis of (+)-And (−)-Aristeromycin[1,2].
Shuto, et al., Tetrahedron Letters, vol. 28, No. 2, pp. 199–202, 1987, A Facile One-Step Synthesis of 5'-Phosphatidylnucleosides.
Kam, et al., J. Org. Chem., 1981, 46, pp. 3268–3272, Carbocyclic Sugar Amines:Synthesis and Stereochemistry of Racemiα-and β-Carbocyclic Ribofuranosylamine, Carbocyclic Lyxofuranosylamine, and Related Compounds.
Temple, et al., J. Org. Chem., vol. 40, No. 21, 1975, p. 3141, Preparation of 2,5-Diamino-4,6-Dichloropyrimidine[1].
Bruce N. Ames, Assays of phosphate and Phosphatases, [10], pp. 115–118, Assay of Inorganic Phosphate, Total Phosphate and Phosphatases.
Paper-J. Med. Chem., 1985, pp. 1385–1386, Resolution of Aristeromycin Enantiomers.
Murray, et al., J. Org. Chem., 1987, 52, pp. 746–748, Chemistry of Dioxiranes, 6, Electronic Effects in the Oxidation of Sulfides and Sulfoxides by Dimethyldioxirane[1].

*Primary Examiner*—Diana Rivers
*Attorney, Agent, or Firm*—Donald Brown; Lawrence A. Nielsen; Hannah O. Green

[57] ABSTRACT

The present invention relates to 6-substituted purine carbocyclic nucleosides and their use in medical therapy particularly in the treatment of HIV and HBV infections. Also provided are pharmaceutical formulations and processes for the preparation of compounds according to the invention.

5 Claims, No Drawings

6-SUBSTITUTED PURINE CARBOCYCLIC NUCLEOSIDES

This is a continuation-in-part of U.S. application Ser. No. 07/371,789, filed June 27, 1989, now abandoned.

The present invention relates to purine nucleoside analogs containing an unsaturated carbocyolic ring in place of the sugar residue, pharmaceutically acceptable derivatives thereof, and their use in medical therapy, particularly for the treatment of certain viral infections.

AIDS is an immunosuppressive or immunodestructive disease that predisposes subjects to fatal opportunistic infections. Characteristically, AIDS is associated with a progressive depletion of T-cells, especially the helper-inducer subset bearing the OKT$^4$ surface marker.

Human immunodeficiency virus (HIV) has been reproducibly isolated from patients with AIDS or with the symptoms that frequently precede AIDS. HIV is cytopathic and appears to preferentially infect and destroy T-cells bearing the OKT$^4$ marker, and it is now generally recognized that HIV is the etiological agent of AIDS.

Since the discovery that HIV is the etiological agent of AIDS, numerous proposals have been made for anti-HIV chemotherapeutic agents that may be effective in treating AIDS sufferers. Thus, for example, U.S. Pat. No. 4,724,232 describes 3'-azido-3'-deoxythymidine (which has the approved name zidovudine), its pharmaceutically acceptable derivatives and their use in the treatment of human retrovirus infections including AIDS and associated clinical conditions. Vince et al., *Antiviral Research*, 9 (1/2), 120 (1988) describes certain carbocyclic nucleoside analogs and their use against HIV. At the Second International Conference on Antiviral Research, Williamsburg, Va., 10–14 April, 1988, (±)-9-(cis-4-(hydroxymethyl)-2-cyclopentenyl)guanine (NSC-614846), also known as carbovir, was disclosed.

Worldwide, hepatitis R virus (HBV) is a viral pathogen of major consequence. It is most common in Asian countries, and prevalent in sub-Saharan Africa. The virus is etiologically associated with primary bepatocellular carcinoma and is thought to cause 80% of the world's liver cancer. In the United States more than ten thousand people are hospitalized for HBV illness each year, an average of 250 die with fulminant disease.

The United States currently contains an estimated pool of 500,000–1 million infectious carriers. Chronic active hepatitis will develop in over 25% of carriers, and often progresses to cirrhosis. It is estimated that 5000 people die from HBV-related cirrhosis each year in the USA, and that perhaps 1000 die from HBV-related liver cancer. Even when a universal HBV vaccine is in place, the need for effective anti-HRV compounds will continue. The large reservoir of persistently infected carriers, estimated at 220 million worldwide, will receive no benefit from vaccination and will continue at high risk for HBV-induced liver disease. This carrier population serves as the source of infection of susceptible individuals perpetuating the instance of disease particularly in endemic areas or high risk groups such as IV drug abusers and homosexuals. Thus, there is a great need for effective antiviral agents, both to control the chronic infection and reduce progression to hepatocellular carcinoma.

Clinical effects of infection with the HRV virus range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease as outlined above. In "Viral Infections of Humans" (second edition, Ed., Evans, A.S. (1982) Plenum Publishing Corporation, New York), Chapter 12 describes in detail the etiology of viral hepatitis infections.

Hepatitis B virus (HRV) is a small DNA containing virus which infects humans. It is a member of the class of closely related viruses known as the hepadnaviruses, each member of which selectively infects either mammalian or avian hosts, such as the woodchuck and the duck. Recent insights into the mechanism of replication of the hepadnavirus genome indicate the importance of reverse transcription of an RNA intermediate, suggesting that the reverse transcriptase is a logical chemotherapeutic target.

It has now been discovered that certain purine nucleoside analogues containing an unsaturated carbocyclic ring, as referred to below, are useful for the treatment of viral infections for example hepatitis R and retroviral infections, especially AIDS.

According to a feature of the present invention, novel compounds of the formula (I) or of formula (Ia) are provided:

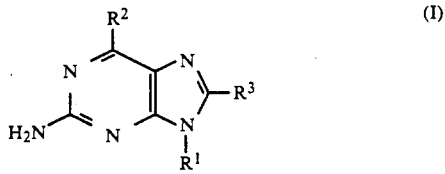

wherein R$^1$ represents

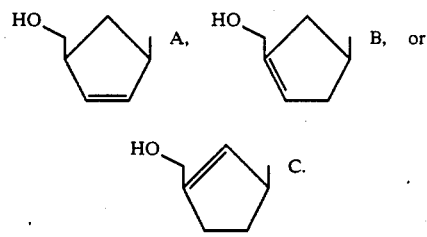

and R$^2$ represents branched or straight chain C$_1$–C$_6$ alkoxy (e.g. propyloxy or isopropoxy) optionally substituted by C$_1$–C$_6$ alkoxy or C$_3$–C$_6$ cycloalkyl (e.g. cyclopropylmethoxy); C$_3$–C$_8$ cycloalkyloxy (e.g. cyclobutyloxy or cyclopentyloxy); C$_4$–C$_8$ cycloalkenyloxy; aryloxy (e.g. phenyloxy); aralkyloxy (e.g. benzyloxy) in which the aryl may optionally be substituted with C$_1$–C$_4$ alkyl, hydroxy or halogen; C$_2$–C$_6$ alkenylthio (e.g. allylthio); C$_3$–C$_8$ cycloalkylthio; C4-8 cycloalkenylthio; C$_1$–C$_6$ branched or straight chain alkyltbio; arylthio or aralkylthio in which the aryl may optionally be substituted with C$_1$–C$_4$ alkyl, hydroxy, halogen or nitro; or R$^2$ represents a heterocyclic group containing an oxygen atom or one or two nitrogen atoms, and 3-7 carbon atoms with optional double bonds in the ring (e.g. piperidino, pyrrolidino or furfuryl) optionally containing one or more heteroatoms selected from sulphur and oxygen and optionally substituted on the ring by one or more C$_1$–C$_4$ alkyl, hydroxy or halogen groups, C$_3$–C$_6$ cycloalkylthio, aralkylthio in which the aryl may be substituted with $C_1$-$C_4$ alkyl, hydroxy or halogen; or $R^2$ represents an imidazolylthio group in which the imidazolyl moiety may be substituted with one or more substituents selected from $C_1$-$C_4$ alkyl and C-substituted with nitro; or $R^2$ represents an amino group which is mono- or di-substituted by one or two substituents selected from branched or straight chain $C_1$-$C_8$ alkyl (e.g. methyl o ethyl) optionally substituted with one or more amino groups, alkylamino groups or $C_1$-$C_6$ alkoxy (e g. methoxyethyl); $C_1$-$C_6$ hydroxyalkyl (e.g. hydroxyethyl); $C_3$-$C_8$ cycloalkenyl (e.g. cyclopenten-1-yl); $C_3$-$C_8$ cycloalkyl (preferably C3-6 cycloalkyl, e.g. cyclopropyl, cyclobutyl or cyclopentyl) optionally substituted by $C_1$-$C_6$ alkyl (e.g. methylcyclopropyl), aryl (e.g. phenylcyclopropyl), aralkyl (e.g. benzyl), halogen (e.g. fluoro) or $C_1$-$C_6$ hydroxyalkyl (e.g. hydroxymethyl); aryl (e.g. phenyl) or aralkyl (e.g. benzyl) in which the aryl may optionally be substituted With $C_1$-$C_4$ alkyl, hydroxy or halogen; allyl optionally substituted with mono- or dialkyl or alkoxy groups (e.g. dimethylallyl); and $R^3$ represents hydrogen, amino, $C_1$-$C_6$ alkyl (e.g. methyl) or thio optionally substituted by $C_1$-$C_6$ alkyl; provided that when $R^1$ is A and $R^3$ is hydrogen or $C_1$-$C_6$ alkyl, $R^2$ is not an amino group substituted by a single $C_3$-$C_8$ cycloalkyl and hydrogen or a branched or straight chain $C_1$-$C_6$ alkyl; or a pharmaceutically acceptable derivative thereof.

Certain compounds of the present invention can be described by formula (Ia)

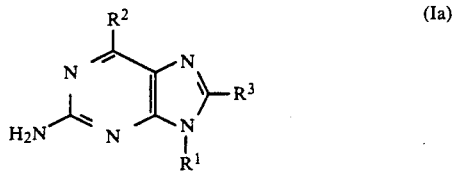

(Ia)

wherein $R^1$ represents

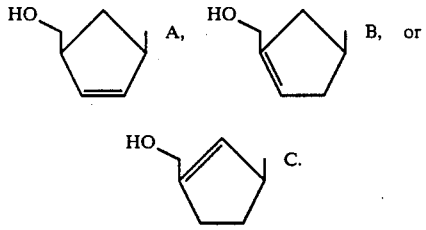

$R^2$ represents cycloalkenyloxy; or $R^2$ represents $C_4$-$C_8$ cycloalkenylthio; or $R^2$ represents an amino group which is mono substituted by any one of $C_1$-$C_8$ branched or straight chain alkyl optionally substituted by one or more amino groups or alkylamino groups; $C_3$-$C_8$ cycloalkenyl (e.g. cyclopenten-1-yl); $C_1$-$C_6$ hydroxyalkyl (e.g. hydroxymethyl); $C_1$-$C_6$ alkyl substituted by $C_3$-$C_8$ cycloalkyl; or $R^2$ represents an amino group which is di-substituted by any one substituent selected from $C_1$-$C_8$ branched or straight chain alkyl optionally substituted by one or more amino groups, alkylamino groups or $C_1$-$C_6$ alkoxy groups; $C_4$-$C_8$ cycloalkenyl; $C_1$-$C_6$ hydroxyalkyl; $C_1$-$C_6$ alkyl substituted by $C_3$-$C_8$ cycloalkyl and any one substituent selected from $C_1$-$C_6$ alkyl (e.g. methyl or ethyl); $C_1$-$C_6$ hydroxyalkyl (e.g. hydroxyethyl); $C_3$-$C_8$ cycloalkyl (preferably $C_3$-$C_6$ cycloalkyl, e.g. cyclopropyl, cyclobutyl or cyclopentyl) optionally substituted by $C_1$-$C_6$ alkyl (e.g. methylcyclopropyl) or aryl (e.g. phenylcyclopropyl); aryl (e.g. phenyl) or aralkyl (e.g. benzyl) in which the aryl may optionally be substituted with $C_1$-$C_4$ alkyl, hydroxy or halogen; allyl optionally substituted with mono- or di-alkyl or alkoxy groups (e.g. dimethylallyl); and $R^3$ represents hydrogen, amino, $C_1$-$C_6$ alkyl (e.g. methyl), or thio optionally substituted by $C_1$-$C_6$ alkyl; provided that when $R^1$ is A and $R^3$ is hydrogen or $C_1$-$C_6$ alkyl, $R^2$ is not an amino group substituted by a single $C_3$-$C_8$ cycloalkyl and hydrogen or a branched or straight chain $C_1$-$C_6$ alkyl; or a pharmaceutically acceptable derivative thereof.

Preferred examples of compounds of formula (I) or of formula (Ia) include those wherein $R^1$ represents A. Also preferred are compounds wherein $R^2$ is $C_1$-$C_6$ alkoxy for example methoxy or butoxy or $R^2$ is $C_1$-$C_6$ alkenyl or alkylthio (e.g. allylthio).

The most preferred isomers are those in which the hydroxymethyl group is cis to the purine in compounds of formula (I) or of formula (Ia). It is to be understood that the present invention encompasses the individual enantiomers of the compounds of formula (I) or of formula (Ia) as well as wholly or partially racemic mixtures of such enantiomers even though the precise structures as drawn relate to one enantiomer.

Particularly preferred examples of compounds of formula (I) are:

a) cis-4-(2-Amino-6-methoxy-9H-purin-9-yl)-2-cyclopentene-1-methanol;
b) cis-4-(2-Amino-6-ethoxy-9H-purin-9-yl)-2-cyclopentene-1-methanol;
c) cis-4-(2-Amino-6-isopropoxy-9H-purin-9-yl)-2-cyclopentene-1-methanol;
d) cis-4-(2-Amino-6-(ethylthio)-9H--purin-9-yl)-2-cyclopentene-1-methanol;
e) cis-4-(6-(Allylthio)-2-amino-9H-purin-9-yl)-2-cyclopentene-1-methanol;
f) cis-4-(2-Amino-6-butoxy-9H-purin-9-yl)-2-cyclopentene-1-methanol;
g) cis-4-(2-Amino-6-cyclopentyloxy-9H--purin-9-yl)-2-cyclopentene-1-methanol;
h) cis-4-(6-(Allylamino)-2-amino-9H-purin-9-yl)-2-cyclopentene-1-methanol;
i) cis-4-(2-Amino-6-propoxy-9H-purin-9-yl)-2-cyclopentene-1-methanol;
j) cis-4-(2-Amino-6-(isobutylthio)-9H-purin-9-yl)-2-cyclopentene-1-methanol;

These compounds are particularly preferred because of the high levels which reach the central nervous system where manifestations of HIV infections ar particularly debilitating.

The compounds of formula (I) or of formula (Ia) above and their pharmaceutically acceptable derivatives are hereinafter referred to as the compounds according to the invention.

In one aspect of the invention there are provided the compounds according to the invention for use in medical therapy particularly for the treatment of retroviral infections and heptatis B Viral infections.

Examples of retroviral infections which may be treated or prevented in accordance with the invention include human retroviral infections such as human immunodeficiency virus (HIV), HIV-1, HIV-2 and human T-cell lymphotropic virus (HLTV), e.g. HTLV-I or HTLV-II infections. The compounds according to the invention are especially useful for the treatment of AIDS and related clinical conditions such as AIDS-related complex (ARC), progressive generalised lymphadenopathy (PGL), AIDS-related neurological conditions, such as multiple sclerosis or tropical paraparesis, anti-HIV antibody-positive and HIV-positive conditions and thrombocytopenic purpura. The compounds may also be used in the treatment or prevention of psoriasis.

The compounds of the present invention are particularly applicable for the treatment of asymptomatic infections or diseases in humans caused by or associated with human retroviruses.

In a further aspect of the present invention there is included:

a) A method for the treatment of retroviral infections and hepatitis B infections which comprises treating the subject with a therapeutically affective amount of a compound according to the invention.

b) Use of a compound according to the invention in the manufacture of a medicament for the treatment of any of the above-mentioned infections or conditions.

By "a pharmaceutically acceptable derivative" is meant any pharmaceutically or pharmacologically acceptable salt, ester or salt of such ester of a compound according to the invention or any other compound which, upon administration to the recipient, is capable of providing (directly or indirectly) a compound according to the invention, or an antivirally active metabolite or residue thereof.

Preferred esters of the compounds of the invention include carboxylic acid esters in which the non-carbonyl moiety of the ester grouping is selected from straight or branched chain alkyl, e.g. n-propyl, t-butyl, n-butyl, alkoxyalkyl (e.g. methoxymethyl), aralkyl (e.g. benzyl), aryloxyalkyl (e.g. phenoxymethyl), aryl (e.g. phenyl optionally substituted by halogen, $C_1-C_4$ alkyl or $C_1-C_4$ alkoxy or amino); sulfonate esters such as alkyl- or aralkylsulfonyl (e.g. methanesulfonyl); amino acid esters (e.g. L-valyl or L-isoleucyl); and mono-, di- or triphosphate esters. The phosphate esters may be further esterified by, for example, a $C_1-C_{20}$ alcohol or reactive derivative thereof, or by a 2,3-di($C_6-C_{24}$)acyl glycerol.

With regard to the above-described esters, unless otherwise specified, any alkyl moiety present advantageously contains 1 to 18 carbon atoms, particularly 1 to 4 carbon atoms. Any aryl moiety present in such esters advantageously comprises a phenyl group. Any reference to any of the above compounds also includes a reference to a pharmaceutically acceptable salt thereof.

Examples of pharmaceutically acceptable salts of the compounds according to the invention and pharmaceutically acceptable derivatives thereof include base salts, e.g. derived from an appropriate base, such as alkali metal (e.g. sodium), alkaline earth metal (e.g. magnesium) salts, ammonium and $NW^+_4$ (wherein W is $C_1-C_4$ alkyl). Physiologically acceptable salts of a hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na+$, $NH_4+$, and $NW_4+$ (wherein W is a $C_1-C_4$ alkyl group).

The above compounds according to the invention and their pharmaceutically acceptable derivatives may be employed in combination with other therapeutic agents for the treatment of the above infections or conditions. Examples of such further therapeutic agents include agents that are effective for the treatment of viral infections or associated conditions such as 3'-azido-3'-deoxythymidine (zidovudine),2',3'-dideoxynucleosides such as 2',3'-dideoxycytidine, 2',3'-dideoxyadenosine and 2',3'-dideoxyinosine, acyclic nucleosides (e.g. acyclovir), interferons such as c-interferon, renal excretion inhibitors such as probenicid, nucleoside transport inhibitors such as dipyridamole, dilazep, mio-, lido- or soluflazine, or hexobendine as well as immunomodulators such as interleukin II and granulocyte macrophage colony stimulating factors, soluble $CD_4$ or genetically engineered derivatives thereof, and phosphonoformic acid. The component compounds of such combination therapy may be administered simultaneously, in either separate or combined formulations, or at different times, e.g. sequentially such that a combined effect is achieved.

The compounds according to the invention, also referred to herein as the active ingredient, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose for each of the above-mentioned conditions (e.g. AIDS) will be in the range of 3.0 to 120 mg per kilogram body weight of the recipient (e.g. a human) per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Ideally the active ingredient should be administered to achieve peak plasma concentrations of the active compound of from about 1 to about 75 $\mu M$, preferably about 2 to 50 $\mu M$, most preferably about 3 to 30 $\mu M$. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient While it is possible for the active ingredient to be administered alone it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous for purine nucleoside derivatives as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulation may be presented in unit-dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

The compounds according to the invention may also be presented for use in the form of veterinary formulations, which may be prepared, for example, by methods that are conventional in the art.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The present invention further includes a process for the preparation of a compound according to the invention and pharmaceutically acceptable derivatives thereof which comprises either:

A) treating a compound of formula (II)

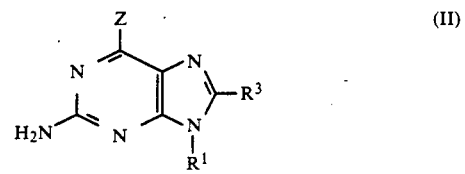

wherein $R^1$ and $R^3$ are as hereinbefore defined and Z represents a precursor group for the said $R^2$ group with an agent or under conditions serving to convert the precursor Z group to the desired $R^2$ group; or Z represents a thio group onto which may be substituted an appropriate group to form a compound of formula (I) or of formula (Ia) wherein $R^2$ is a substituted thio group or;

B) reacting a compound of formula (III)

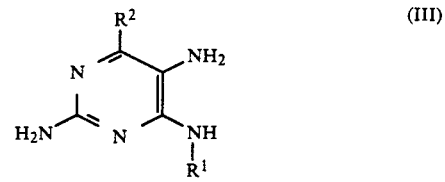

(wherein $R^1$ and $R^2$ are hereinbefore defined) or a pharmaceutically acceptable derivative thereof, with an agent serving to effect formation of the imidazole ring in the desired compound of formula (I) or of formula (Ia); or i) where a compound of formula (I) or of formula (Ia) Is formed, converting the said compound to a pharmaceutically acceptable derivative thereof; or ii) where a pharmaceutically acceptable derivative of a compound of formula (I) or of formula (Ia) is formed, converting the said derivative to the parent compound of formula (I) or of formula (Ia) or to a further such derivative.

Process A) above may be carried out in conventional manner, for example, by treatment of a compound of formula (II) in which Z represents a leaving group (e.g. a halo such as a chloro group) with, for example, an alkali metal (e.g. sodium) or alkali metal hydride (e.g. sodium hydride) and an appropriate alcohol at reflux or a temperature greater than 50° C. preferably in an organic solvent.

Alternatively the compound of formula (II) may be treated with an appropriate amine or amino hydrochloride to introduce a substituted amino group as defined above at reflux or at a temperature greater than 50° C. preferably in the presence of an organic solvent, for example methanol, ethanol. Alternatively, a compound of formula (II) wherein Z is a thio group may be treated with an appropriate halide under nitrogen.

Process B) may be carried out, for example, by reacting a compound of formula (III) with formic acid or a reactive formic acid derivative (e.g. triethylorthoformale or diethoxymethyl acetate) in a solvent such as a dimethylacetamide or dimethylformamide at an elevated temperature, preferably at 75-90° C. This reaction is conveniently effected by the addition of slightly more than one equivalent of a strong anhydrous acid, e.g. with 1.1 equivalents of ethanesulfonic acid per equivalent of compound of formula (III), in which case lower temperatures (e.g., 25° C.) are used.

In process A) the starting material of formula (II) may be prepared, for example, by firstly cyclizing a compound of formula (III) above in an analogous manner to that described for process B) above.

Alternatively, (1R,4S)-9-(4-hydroxymethyl-2-cyclopentenyl)guanine, prepared, e.g. as described in Australian patent application No. AU-A-28671/89 (incorporated herein by reference) from aristeromycin, may be converted to compounds of formula (I) or of formula Ia).

Other reagents may be useful for cyclisation of compounds of formula (III) to give compounds of formula (I) or of formula (Ia) where $R^3$ is not hydrogen. For example triethyl or trimethylorthoacetate with acetic anhydride at 70-120° C. for several hours gives $R_3=CH_3$ (see H. C. Koppel and R. K. Robins, *J. Org. Chem.* 1958. 1457), $R_3=NH_2$ may be obtained by cyclisation with ethoxycarbonyl isothiocyanate (see R. Esmail and F. Kurzer, *Synthesis* 1975, 301; L. B Towsend, et al., *J. Heterocyclic Chem.* 1984, 21, 1245). This aqueous sodium hydroxide) to $R^3=NHO_2$. Cyclization with potassium ethylxanthate (W. T. Stolle, J. C. Sih, R.S.P. Hsi, *J. Label. Compound Radiopharm.* 1988, 891) In ethanol at 80° C. gives $R^3=SH$. Alkylation of the SH with alkyl halides and base (e.g. potassium carbonate in DMF) gives $R^3=SMe$, SEt.

A compound of formula (I) or of formula (Ia) may be converted into a pharmaceutically acceptable ester by reaction with an appropriate esterifying agent, e.g. an acid halide or anhydride. The compound of formula (I) or of formula (Ia), including esters thereof, may be converted into pharmaceutically acceptable salts thereof in conventional manner, e.g. by treatment with an appropriate acid. An ester or salt of a compound of formula (I) or of formula (Ia) may be converted into the parent compound, e.g. by hydrolysis.

The enantiomers of the compounds of formula (I) or of formula (Ia) may be resolved or isolated in conventional manner, e.g. by chromatographic separation of diastereomeric esters prepared by acylation of the hydroxyl on the cyclopentenyl moiety with appropriate optically active carboxylic acid derivatives as, e.g., with naproxen (*J. Org. Chem.* 1986, 51, 1287). The cyclopentenyl precursors of the compounds of formula (III) may also be resolved by fractional crystallization of salts formed with optically active carboxylic acids (e.g. dibenzoyl-D-tartaric acid). Alternatively, enzymatic resolution may be achieved as in *J. Med. Chem.* 1987, 30, 746 and *J. Med. Chem.* 1985, 28, 1385.

The following Examples are intended for illustration only and are not intended to limit the scope of the invention in any way. The term 'active ingredient' as used in the Examples means a compound of formula (I) or of formula (Ia) or a pharmaceutically acceptable derivative thereof.

EXAMPLE 1

(+)-cis-4-[(2-Amino-4-chloro-6-pyrimidinyl)amino]-2-cyclopentene-1-methanol cis-4-Acetamidocyclopent-2-enemethyl acetate (U.S. Pat. No. 4,268,672) (14.88 g, 0.073 mol) and barium hydroxide octahydrate (46.19 g, 0.146 mol) were refluxed in water (300 mL) under nitrogen for 18 hours. The resulting solution was neutralized with carbon dioxide. The precipitate was washed with water, then ethanol. The combined filtrate-wash was evaporated to a syrup (11.16 g) which was condensed with 2-amino-4,6-dichlorpyrimidine (23.91 g, 0.146 mol) and triethylamine (30.5 mL, 0.219 mol) in refluxing 1-butanol (100 mL) for 1.5 hours. After addition of 1 N NaOH (73 mL), the resulting mixture was evaporated to dryness and the residual solid slurried in CHCl$_3$ (200 mL). Unreacted 2-amino-4,6-dichloropyrimidine was filtered off and washed with chloroform (100 mL). The chloroform filtrate-wash was concentrated and chromatographed on a silica gel column. Additional pyrimidine starting material was eluted with 2.5% methanol-chloroform. The title compound was eluted with 3.5% methanol-chloroform as an off-white solid foam (15.90 g, 91%).

$^1$H-NMR; (Me$_2$SO-d$_6$) δ 1.15–1.28 and 2.26–2.41 (2m, 2, CH$_2$); 2.60–2.71 (m, 1, 1'-H); 3.4 (m overlapping H$_2$O, CH$_2$OH); 4.625 (t, J=5.3, 1, CH$_2$OH); 4.95 (br s, 1, CH—N); 5.67–5.87 (m, 2, CH=CH); 6.38 (br s, i, NH$_2$); 7.12 (br s, 1, NH); MS (CP) M+1, 241, 243.

Anal Calcd. for C$_{10}$H$_{13}$N$_4$OCl·0.2 H$_2$O: C, 48.99; H, 5.55; N, 22.85; Cl, 14.46.

Found: C, 49.10; H, 5.57; N, 22.81; Cl, 14.40.

EXAMPLE 2

(±)-cis-4-[[2-Amino-6-chloro-5-[(4-chlorophenyl)azo]-4-pyrimidinyl]-amino]-2-cyclopentene-1-methanol (±)-cis-4-[(2-Amino-4-chloro-6-pyrimidinyl)amino]-2-cyclopentene-1-methanol from Example 1 (11.58 g, 48 1 mmol) and sodium acetate trihydrate (97 g) were dissolved in glacial acetic acid (225 mL) and water (225 mL). A cold solution (0.5° C.) of 4-chlorobenzenediazonium chloride was prepared from 4-chloroaniline (6.74 g, 52.8 mol), concentrated hydrochloric acid (14.7 mL) water (52 mL), and sodium nitrite (4.01 g, 58.2 mmol in 47 mL of water). This cold solution was added dropwise over 5 minutes to the first solution. The resulting yellow precipitate was filtered after 18 hours, washed with water, and extracted with ethanol to give title compound as dark yellow powder (12.56 g, 69%), m.p. 218-220° C. dec.

$^1$H-NMR: (Me$_2$SO-d$_6$) δ 10.25 (d, 1, NH); 7.69 and 7.54 (both, J=8.9, C$_6$H$_4$) overlapping 7.6 (br, 6, NH$_2$); 5.80–5.95 (m, 2, CH=CH); 5.24 (m, 1, CHN); 4.75 (t, 1, CH$_2$OH); 3.41 (t, 1, CH$_2$OH); 3.41 (t, 2, CH$_2$OH); 2.75 (m, 1, CH); 2.41 (m, 1, CH); 1.44–1.53 (m, 1, CH).

Anal. Calcd. for C$_{16}$H$_{16}$N$_6$Cl$_2$O: C, 50.67; H, 4.25; N, 22.16; Cl, 18.70.

Found: C, 50.59; H, 4.29; N, 22.10; Cl, 18.66.

EXAMPLE 3

(±)-cis-4-[(2,5-Diamino-4-chloro-6-pyrimidinyl)-amino]-2-cyclopenlene-1-methanol The title compound of Example 2 (11.67 g) was suspended in ethanol (235 mL), glacial acetic acid (30 mL), and water 235 mL). The mixture was heated to reflux under nitrogen. Zinc dust (13.5 g) was added in small portions over 30 minutes during which time the compound dissolved. The reaction was heated an additional 20 minutes, and then the excess zinc was filtered of from the hot solution, and it was washed with ethanol. The filtrates were evaporated, and the residue was purified on a silica gel column eluting with chloroform (1 L) and chloroform:methanol/4:1 (1.8 L) The fractions containing the product were combined, and the solvent was removed under reduced pressure to give the title compound as a red-orange oil (11.2 g, >100% yield). A pure sample was obtained during another small scale reaction to obtain the product as a light yellow solid in a 76% yield.

$^1$H-NMR: (Me$_2$SO-d$_6$) δ 1.29 and 2.39 (m, 2, CH$_2$); 2.69 (t, 1, 1'-H); 3.37 (d, 2, CH$_2$OH); 3.91 (br, 2, NH$_2$); 4.60 (br, 1, CH$_2$OH); 5.02 (m, 1, CHNH); 5.56 (br s, 2, NH$_2$); 5.74 (m, 1, =CH); 5.86 (m, 1, =CH); 6.36 (d, 1, CHNH).

EXAMPLE 4

(±)-cis-4-(2-Amino-6-chloro-9H-purin-9-yl)-2-cyclopentene-1-methanol

The title compound of Example 3 (about 9.7 g) was dissolved in diethoxymethyl acetate (100 g), and refluxed for two days. The solvent was removed under high vacuum at 50° C., and dioxane (40 mL) and 0.5 N HCl (60 mL) was added. The reaction was stirred at room temperature for 1.25 hours, and then chilled. The reaction was neutralized to pH 7 with cold 5 N sodium hydroxide, and then it was extracted with chloroform:methanol/3:1 several times. The organic layers were dried with magnesium sulphate, filtered, and evaporated. The residue was purified by chromatography on a silica gel column, eluting with CHCl$_3$: 2% MeOH to give 3.7 g (46% yield) of the title compound, m.p 138-139° C.

$^1$H-NMR: (Me$_2$SO-d$_6$) δ 1.63 and 2.61 (m, 2, CH$_2$); 2.87 (m, 1, 1'-H); 3.44 (d, 2, CH$_2$OH); 5.44 (m, 1, CH-N); 5.89 (m, 1, =CH); 6.14 (m, 1, =CH); 6.82 (br s, 2, NH$_2$); 8.02 (s, 1, 8-H); (CH$_2$OH not seen - under H$_2$O peak). UV: pH 1 λmax 315 (ε 7370); 218 (26200); λ sh 239.5 (5650). pH 7.4 λmax 307 (ε 8000); 245.5 (4600); 223 (26400). MS (E1) 265,267 (m) (Cl) 266,268 (m+1).

Calcd for C$_{11}$H$_{12}$N$_5$Cl0.2H$_2$O: C, 43.79; H, 5.35; N, 23.21; Cl, 11,75.

Found: C, 43.67; H, 5.29; N, 23.05; Cl, 11.70.

EXAMPLE 5

(±)-cis-4-(2-Amino-6-methoxy-9H-purin-9-yl)-2-cyclopentene-1-methanol (±)-cis-4-(2-Amino-4-chloro-9H-purin-9-yl)-2-cyclopentene-1-methanol from Example 4 (0.53 g, 2.0 mmol) was dissolved in methanol (25 mL) and a solution of sodium (0.23 g, 10 m.equiv.) and methanol (20 mL) added. After 1.0 hour of reflux, the solution was cooled, neutralized with hydrochloric acid. Evaporated solvent and chromatographed residue on silica gel. Product was eluted as a white solid foam (0.44 g) with 5% methanol-ethylacetate.

$^1$H-NMR: (Me$_2$SO-d$_6$) δ 1.57 and 2.60 (both m, 2, CH$_2$); 2.85 (m, 1, 1'-H); 3.43 (t, 2, CH$_2$OH); 3.94 (s, 3, OCH$_3$); 4.70 (t, 1, CH$_2$OH); 5.42 (m, 1, CH—N); 5.86 and 6.11 (m, 2, CH=CH); 6.37 (s, 2, NH$_2$); 7.75 (s, 1, purine-8H).

Anal. Calcd. for C$_{12}$H$_{15}$N$_5$O$_2$.0.05 EtOAc·0.2 H$_2$O·0.30 MeOH; C, 53.83; H, 6.14; N, 25.11.

Found: C, 53.87; H, 6.09; N, 25.07.

EXAMPLE 6

(±)-cis-4-(2-Amino-6-ethoxy-9H-purin-9-yl)-2-cyclopentene-1-methanol

A flask was charged with ethanol (33 ml) and sodium (0.172 g, 7.5 mmol). After all of the sodium had dissolved (±)-cis-4-(2-amino-6-chloro-9H-purin-9-yl)-2-cyclopentene-1-methanol (0.40 g, 1.5 mmol) from Example 4 was added and the solution was brought to reflux for 0.5 hours. The solution was allowed to cool to room temperature before neutralization with 1.0 N HCl. The solution was then concentrated and the residue partitioned between chloroform and water. The organic layer was dried with MgSO$_4$, filtered and concentrated. The residues were then placed on a silica gel column and eluted with 2% methanol in chloroform to yield a yellow glass (0.28 g, 67.8%).

$^1$H-NMR: (Me$_2$SO-d$_6$) δ 7.74 (s, 1H, purine H-8); 6.35 (br s, 2H, NH$_2$); 6.15 and 6.07 and 5.91-5.82 (both m, 2H, CH=CH); 5.49-5.35 (br m, 1H, CHN); 4.71 (t, J=5.3 Hz, 1H, OH); 4.43 (a, J=7.0 Hz, OCH$_2$ CH$_3$); 3.50-3.39 (m, 2H, OCH$_2$); 2.95-2.78 (br m, 1H, H-1'); 2.70-2.52 (br m, overlapping solvent, 0.5 CH$_2$); 1.68-1.52 (br m, 1H, 0.5 CH$_2$); 1.33 (+, J=7.1 Hz, 3H, CH$_3$).

Anal. Calcd. for C$_{13}$H$_{17}$N$_5$O$_2$: C, 56.72; H, 6.22; N, 25.44.

Found: C, 56.48; H, 6.28; N, 25.20.

EXAMPLE 7

(±)-cis-4-(2-Amino-6-isopropoxy-9H-purin-9-yl)-2-cyclopentene-1-methanol

A flask was charged with sodium hydride (60% oil dispersion, 240 mg, ~6 mmol) which was washed with hexanes before the addition of isopropanol (20 mL) and (±)-cis-4-(2-amino-6-chloro-9H-purin-9-yl)-2-cyclopentene-1-methanol (0.318 g, 1.19 mmol) from Example 4. This solution was heated at 75° C. for 2 hours before being allowed to cool to room temperature and neutralized by addition of 1.0 N HCl. The solution was concentrated and the residue was placed on a silica gel column which was eluted with 10% methanol-chloroform. Crystallization from ethanol:water 1:1 yielded off-white crystals (265 mg, 77%), m.p. 188-191° C.

$^1$H-NMR: (Me$_2$SO-d$_6$) δ 7.72 (s, 1H, purine H-8); 6.28 (s, 2H, NH$_2$); 6.09 and 5.87 (both m, 2H, CH=CH); 5.50-5.37 (m, 2H, CHN, CHO); 4.69 (t, J=5.3, 1H, OH); 3.43 (m, 2H, CH$_2$OH); 2.86-2.81 (br m, 1H, CH); 2.67-2.51 and 1.64-1.52 (2m, 2H, CH$_2$); 1.31 (d, J=6.2, (CH$_3$)$_2$CH).

Anal. Calcd. for C$_{14}$H$_{19}$N$_5$O$_2$; C, 58.12; H, 6.62; N, 24.20.

Found C, 58.20; H, 6.66; N, 24.20.

EXAMPLES 8 AND 9

(±)-cis-2-Amino-1,9-dihydro-9-[(4-hydroxymethyl)-2-cyclopenten-1-yl]-6H-purin-6-thione and (±)-cis-4-(2-Amino-6-(propylthio)-9H-purin-9-yl)-2-cyclopenten-1-methanol (±)-cis-4-(2-Amino-6-chloro-9H-purin-9-yl)-2-cyclopenten-1-methanol (4.18 g, 15.7 mmol) from Example 4 and thiourea (1.32 g, 17.3 mmol) were refluxed in n-propanol for 17 hours. The resulting mixture was filtered and the solid washed with n-propanol to give (±)-cis-2-amino-1,9-dihydro-9-[(4-hydroxymethyl)-2-cyclopentenyl)-6H--purin-6-thione as yellow powder (2.19 g, 53%), m.p. 235-238° C.

$^1$H-NMR: (DMSO-d$_6$) δ 11.85 (5, 1, NH); 7.77 (s, 1, H-8); 6.76 (br s, 2 NH$_2$); 6.16 and 5.86 (both m, 2, CH=CH); 5.35 (m, 1, CH—N); 4.70 (m, 1, OH); 3.42 (br m, overlapping H$_2$O, CH$_2$-O); 2.85 (br m, 1, CH); 2.30 (m, overlapping solvent, 0.5 CH$_2$); 1.60 (m, 1, 0.5 CH$_2$).

Anal. Calcd. for C$_{11}$H$_{13}$N$_5$O$_5$: C, 50.18; H, 4.98; N, 26.60; S, 12.18.

Found: C, 50.10; H, 5.00; N, 26.50; S, 12.10.

Chromatography on silica gel of the propanol filtrate contents gave a second product on elution with 5% MeOH-EtOAc Crystallization from acetonitrile gave (±)-cis-4-(2-amino-6-propylthio-9H-purin-9-yl)-2-cyclopenten-1-methanol as a yellow powder (0.441 g, 10%), m.p. 128-130° C.

$^1$H-NMR: (DMSO-d$_6$) δ 7.84 (s, 1, H-8); 6.46 (br s, 2, NH$_2$); 6.15 and 5.90 (both m, 2, CH=CH); 5.45 (br m, 1, CH—N); 4.73 (t, J=5.4, 1, OH); 3.45 (m, 2, CH2-0); 3.25 (t, J=7.3, 2, s-CH$_2$); 2.90 (br m, 1, CH); 2.70-2.55 (m, 1, 0.5 CH$_2$); 1.80-1.50 (m, 3, 0.5 CH$_2$ overlapping CH$_2$ of propyl); 1.0 (t, J-7.3, 3, CH$_b$ 3).

Anal. Calcd. for C$_{14}$H$_{19}$N$_5$O$_5$: C, 55.06; H, 6.27; N, 22.93; S, 10.50.

Found: C, 55.15; H, 6.25; N, 22.91; S, 10.58.

EXAMPLE 10

(±)-cis-4-(2-Amino-6-(methylthio)-9H-purin-9-yl)-2-cyclopenten-1-methanol

A solution of (±)-cis-2-amino-1,9-dihydro-9-[(4-hydroxymethyl)-2-cyclopentenyl)]-6H-purin-6-thione (0.50 g, 1.89 mmol) from Example 4 in 1 N NaOH (1.89 mL) was stirred under N$_2$ with methyliodide (0.54 g, 3.79 mmol) for 30 minutes. The mixture was extracted with CHCl$_3$ (3×100 ml). Extracts were dried (MgSO$_4$), solvent evaporated and the residual solid chromatographed. Product was eluted from a silica gel column with 10% MeOH-CHCl$_3$. Crystallization of such a sample from acetonitrile gave title compound as yellow crystals (0.410 g, 78%), m.p. 152-154° C.

$^1$H-NMR: (DMSO-d$_6$) δ 7.84 (s, 1, H-8); 6.49 (br s, 2, NH$_2$); 6.15 and 5.90 (both m, 2, CH=CH); 5.45 (br m, 1, CH—N); 4.73 (t, J=5.3, 1, OH); 3.45 (m, 2, CH$_2$O); 2.90 (br m, 1, CH); 2.70-2.55 (m, overlapping s at 2.57, 4, 0.5 CH$_2$ and CH$_3$); 1.65-1.55 (m, 1, 0.5 CH$_2$).

Anal. Calcd. for C$_{12}$H$_{15}$N$_5$OS: C, 51.97; H, 5.45; N, 25.25; S, 11.56.

Found: C, 51.98; H, 5.48; N, 25.21; S, 11.65.

EXAMPLE 11

(±)-cis-4-(2-Amino-6-((4-nitrobenzylthio)-9H-purin-9-yl)-2-cyclopenten-1-methanol A solution of (±)-cis-2-amino-1,9-dihydro-9-[(4-hydroxymethyl-2-cyclopentenyl)-6H-purin-6-thione (0.50 g, 1.89 mmol) from Example 8 in DMF (5 mL) was stirred with K$_2$CO$_3$ (0.26 g, 1.89 mmol) and p-nitrobenzylbromide (0.41 g, 1.89 mmol) under nitrogen for 12 hours. The mixture was partitioned between H$_2$O (5 mL) and CHCl$_3$ (3×50 mL). The CHCl$_3$ extracts were dried (MgSO$_4$), concentrated to a yellow oil, and the oil chromatographed. Elution of a silica gel column with 10% MeOH-CHCl$_3$ gave title compound as a yellow powder (0.545 g, 73%), m.p. 199-201° C.

$^1$H-NMR; (DMSO-d$_6$) δ 8.15 (AB, J=8.8H$_2$, 2, 0.5 C$_6$H$_4$); 7.76 (AB, J=9.0, 2, 0.5 C$_6$H$_4$); 7.83 (s, 1, H-8); 6.62 (s, 2, NH$_2$); 6.10 and 5.85 (both m, 2, CH=CH); 5.40 (hr m, 1, CH—N); 4.70 (t, J=5.3, 1, OH); 4.63 (s, 2, CH$_2$-S); 3.42 (m, 2, CH$_2$O); 2.85 (br m, 1, CH); 2.70-2.50 (m, overlapping solvent, 0.5 CH$_2$); 1.70-1.50 (m, 1, 0.5 CH$_2$).

Anal. Calcd. for C$_{18}$H$_{18}$N$_6$O$_3$S: C, 54.26; H, 4.55; N, 21.09; S, 8.05.

Found: C, 54.17; H, 4.56; N, 21.05; S, 8.11.

EXAMPLE 12

(±)-cis-4-(2-Amino-6-((1-methyl-4-nitro-1H-imidazol-5-yl)thio)-9H-purin-9-yl)-2-cyclopenten-1-methanol To a solution of (±)-cis-2-amino-1,9-dihydro-9-[(4-hydroxymethyl)-2-cyclopenten-1-yl)-6H-purin-6-thione (0.50 g, 1.89 mmol) from Example 8 in 1N NaOH (1.89 mL) was added 1-methyl-4-nitro-5-chloroimidazole (0.31 g, 1.89 mmol). The solution was stirred under nitrogen overnight and the resulting precipitate filtered after addition of H$_2$O (3 mL). Chromatography of the precipitate on silica gel gave title compound, eluted with 10% MeOH-CHCl$_3$ as yellow powder (0.638, 87%), m.p. 207-208° C.

$^1$H-NMR: (DMSO-d$_6$) 4 8.19 (s, 1 imidazolyl CH); 7.89 (s, 1, H-8); 6.55 (br, s, 2, NH$_2$); 6.15 and 5.85 (both m, 2, CH=CH); 5.40 (br m, 1, CH—N); 4.70 (t, J=5.3 Hz, 1, OH); 3.65 (s, 3, CH$_3$); 3.40 (m, 2, OCH$_2$); 2.85 (br m, 1, CH); 2.70-2.50 (m, overlapping solvent, 0.5 CH$_2$); 1.70-1.50 (m, 1, 0.5 CH$_2$).

Anal. Calcd. for C$_{15}$H$_{16}$NO$_3$S·1H$_2$O: C, 44.33; H, 4.46; N, 27.57; S, 7.89.

Found: C, 44.22, 44.12; H, 4.46, 4.49; N, 27.52, 27.46; S, 7.81.

EXAMPLE 13

(±)-cis-4-(2-Amino-6-(ethylthio)-9H-purin-9-yl)-2-cyclopenten-1-methanol

To a solution of (±)-cis-2-amino-1,9-dihydro-9-[(4-hydroxymethyl)-2-cyclopentenyl)-6H-purin-6-thione (0.50 g, 1.89 mmol) in 1 N NaOH (1.89 mL) was added ethyliodide (0.29 g, 1.89 mmol) and dioxane (1 mL). The solution was stirred at 25° C. under nitrogen for 1.25 hours. The resulting mixture was extracted with CHCl$_3$ (3×50 mL), dried (MgSO$_4$) and evaporated to give crude product as yellow oil. Chromatography on silica gel gave title compound eluted with 10% MeOH-CHCL$_3$ and solidified to yellow powder in acetonitrile (0.445 g, 80%), m.p. 123-125° C.

$^1$H-NMR (DMSO-d$_6$) 4 7.82 (s, 1, H-8), 6.43 (br, s, 2, NH$_2$); 6.15 and 5.85 (both m, 2, CH=CH), 5.43 (m, 1, CH—N), 4.70 (t, J=5.4, 1, OH); 3.43 (m, 2, CH$_2$O); 3.23 (q, J=7.3, overlapping H$_2$O, S-CH$_2$); 2.85 (br m, 1, CH); 2.70-2.55 (m, 1, 0.5 CH$_2$); 1.70-1.50 (m, 1, 0.5 CH$_2$); 1.30 (t, J=7.3, 3, CH$_3$).

Anal. Calcd. for C$_{13}$H$_{17}$N$_5$OS: C, 53.51; H, 5.83; N, 24.19; S, 10.99.

Found: C, 53.32; H, 5.93; N, 24.00; S, 10.94.

EXAMPLE 14

(±)-cis-4-(2-Amino-6-(allylthio)-9H-purin-9-yl)-2-cyclopenten-1-methanol

To a solution of (±)-cis-2-amino-1,9-dihydro-9-[(4-hydroxymethyl)-2-cyclopentenyl]-6H-purine-6-thione (0.50 g, 1.89 mmol) from Example 8 in 1 N NaOH (1.89 mL), was added allylbromide (0.229 g, 1.89 mmol) and dioxane (1 mL). The solution was stirred at 25° C. under nitrogen for 1 hour. The mixture was extracted with CHCl$_3$ a yellow oil. Chromatography on silica gel gave the title compound, which was eluted with 10% MeOH-CHCl$_3$ and solidified to yellow powder in acetonitrile, (0.436 g, 76%), m.p. 108-110° C.

$^1$H-NMR: (DMSO-d$_6$) δ 7.83 (s, 1, H-8); 6.49 (br s, 2, NH$_2$); 6.15 and 5.85 (both m, overlapping 6.0, m, total 3, CH=CH, and CH=CH$_2$); 5.45 (m, overlapping dd centered at 5.35, 2, CH—N, and 0.5=CH$_2$); 5.10 (dd, 1, 0.5=CH$_2$); 4.70 (t, J=5.3 Hz, 1, OH), 3.95 (d, J=6.8 Hz, 2, S-CH$_2$), 3.45 (m, 2, CH$_2$O), 2.85 (br m, 1, CH), 2.60 (m, 1, 0.5 CH$_2$), 1.60 (m, 1, 0.5 CH$_2$).

Anal. Calcd. for C$_{14}$H$_{12}$N$_5$OS: C, 55.42; H, 5.65; N, 23.08; S, 10.57.

Found: C, 55.37; H, 5.70; N, 23.03; S, 10.47.

EXAMPLE 15

(±)-cis-4-(2-Amino-6-((2-cyclohexen-1-yl)thio)-9H-purin-9-yl)-2-cyclopenten-1-methanol To a solution of (±)-cis-2-amino-1,9-dihydro-9-[(4-hydroxymethyl)-2-cyclopentenyl]-6H-purine-6-thione (0.50 g, 1.89 mmol) from Example in 1 N NaOH (1.89 ml) was added 3-bromocyclohexene (0.305 g, 1.89 mMol) and dioxane (2 mL). The solution was stirred under nitrogen for 2 hours and extracted with CHCl$_3$ (3×50 mL). CHCl$_3$ extracts were dried (MgSO$_4$) and concentrated to yellow oil. Chromatography on silica gel gave title compound, which was eluted with 10% MeOH-CHCl$_3$ and solidified to a yellow powder in acetonitrile (0.263 g, 41%), m.p. 138-140° C.

$^1$H-NMR: (DMSO-d$_6$) a 7.82 (s, 1, H-8); 6.46 (br s, 2, NH$_2$); 6.15 and 5.85 (both m, overlapping 5.90-5.70, m, total 4, 2',3' and cyclohexene CH=CH); 5.40 (m, 1, CH—N); 4.90 (br m, 1, S-CH); 4.70 (t, J=5.3, 1, OH); 3.45 (m, 2, CH$_2$-O); 2.85 (br m, 1, CH); 2.70-82.55 (m, 1, 0.5 CH$_2$); 2.10-1.50 (m, 7, 3 CH$_2$ plus 0.5 CH$_2$)

Anal. calc. for C$_{17}$M$_{21}$N$_5$OS: C, 59.45; H, 6.16; N, 20.39; S, 9.34.

Found: C, 59.17; H, 6.18; N, 20.31; S, 9.25.

EXAMPLE 16

(±)-cis-4-(2-Amino-6-butoxy-9H-purin-9-yl)-2-cyclopentene-1-methanol

A flask was charged with sodium hydride (60% oil dispersion 300 mg, 7.5 mmol) which was then washed with hexanes before the addition of butanol (10 mL) containing (±)-cis-4-(2-amino-6-chloro-9H-purin-9-yl)-2-cyclopentene-1-methanol (800 mg, 3 mmol) from Example 4. The solution was stirred at reflux for 2 hours and then neutralized by the addition of 1.0 N NaOH. Concentration of the solution afforded the crude product which was purified by elution from a silica gel column with 5% methanol-chloroform; (810 mg, 94%). Crystallization of such a sample from ethanol/acetonitrile gave an off-white powder, m.p. 122-123° C.

$^1$H-NMR: (Me$_2$SO-d$_6$) δ 7.73 (s, 1H, purine H8); 6.12 and 5.86 (m, 2H, CH=CH); 5.41 (br m, 1H, NCH); 4.71 (unresolved t, 1H, OH); 4.38 (t, J=6.6 Hz, 2H, OCH$_2$ butyl); 3.42 (m, 2H, OCH$_2$); 2.85 (br m, 1H, CH); 2.60 (m, 1H, 0.5CH$_2$ cyclopentene); 1.75-1.35 (m, 5H, 0.5CH$_2$ cyclopentene, CH$_2$ CH$_2$); 0.92 (t, J=7.3Hz, 3H, CH$_3$).

Anal. Calcd. for C$_{15}$H$_{21}$N$_5$O$_2$: C, 59.39; H, 6.98; N, 23.09.

Found: C, 59.56; H, 7.07; N, 22.87.

EXAMPLE 17

(±)-cis-4-(2-Amino-6-cyclopentyloxy-9H-purin-9-yl)-2-cyclopentene-1-methanol

A flask was charged with sodium hydride (60% oil dispersion, 185 mg, 4.6 mmol) which was then washed with hexanes before the addition of cyclopentanol (10 mL). The resulting mixture was heated and (±)-cis-4-(2-Amino-6-chloro-9H-purin-9-yl)-2-cyclopentene-1-methanol (0.53 g, 2 mmol) from Example 4 was added. After stirring at 100° C. for 0.75 hours the solution was neutralized by the addition of 1.0 N HCl. Concentration of the solution afforded the crude product which was purified by elution from a silica gel column with 5% methanol-chloroform (0.30 g, 47.6%). Crystallization of such a sample from ethanol-acetonitrile gave an off white powder: m.p. 188-190° C.

$^1$H-NMR: (Me$_2$SO-d$_6$) δ 7.74 (s, 1H, purine H8); 6.33 (br s, 2H NH$_2$); 6.12 and 5.87 (m, 2H, CH=CH); 5.60 (m, 1H, OCH); 5.42 (m, 1H, NCH); 4.73 (t, J=5.1 Hz, 1H, OH); 3.44 (m, 2H, OCH$_2$); 2.87 (br m, 1H, CH); 2.63-2.57 (m, 1H, 0.5 CH$_2$ cyclopentane); 1.98 (br m, 2H, cyclopentane); 1.80-1.57 (br m, 7H, 0.5 CH$_2$ cyclopentene, 3CH$_2$).

Anal. Calcd. for C$_{16}$H$_{21}$N$_5$O$_2$: C, 60.94; H, 6.71; N, 22.21.

Found: C, 60.99; H, 6.73; N, 22.20.

EXAMPLE 18

(±)-cis-4-(2-Amino-6-(allylamino)-9H-purin-9-yl)-2-cyclopentene-1-methanol (±)-(1α, 4α)-4-(2-Amino-6-chloro-9H-purin-9-yl)-2-cyclopentene-1-methanol (0.531 g, 2 mmol) from Example 4, allylamine (1.014 g, 17.8 mmol) and ethanol (5 mL) were stirred at reflux for 2.75 hours. The solution was allowed to cool to room temperature before the addition of 2.0 mL of 1 N NaOH. Evaporation afforded the crude product which was purified by elution from a silica gel column with 5% methanol - chloroform (0.36 g, 63%). Crystallization of such a sample from ethanol yielded an off white powder, m.p. 181-183° C.

$^1$H-NMR: (Me$_2$SO-d$_6$) δ 7.58 (s, 1H, purine H.8); 7.28 (br 2, 1H, NH); 6.11-6.06 (m, 1H, 0.5 CH=CH); 5.98-5.82 (m overlapping br s at 5.86, 4H 0.5 CH=CH, CH=, NH$_2$); 5.37 (m, 1H, NCH); 5.16-4.98 (m, 2H, =CH$_2$); 4.72 (t, J=5.1 Hz, 1H, OH); 4.07 (br m, 2H, NCH$_2$); 3.42 (m, 2H, OCH$_2$); 2.84 (br m, 1H, CH); 2.65-2.54 and 1.62-1.57 (m, 2H, cyclopentyl CH$_2$).

Anal. Calcd. for C$_{14}$H$_{18}$N$_6$O: C, 58.73; H, 6.34; N, 29.35.

Found: C, 58.47; H, 6.42; N, 29.19.

EXAMPLE 19

(±)-cis-4-(2-Amino-6-morpholino-9H-purin-9-yl)-2-cyclopentene-1-methanol

A solution of (±)-cis-4-(-2-Amino-6-chloro-9H-purin-9-yl)-2-cyclopentene-1-methanol (0.531 g, 2.00 mmol) from Example 4 and morpholine (0.526 g, 6.04 mmol) in ethanol (6 mL) was stirred at reflux for 1 hour. The reaction mixture was allowed to cool to room temperature before the addition of 2 mL of 1.0 N NaOH. Concentration of the mixture afforded the crude product which was purified by elution from a silica gel column using 5% methanol in chloroform (0.62 g, 98%). Crystallization of such a sample from ethanol-water gave a white powder; m.p. 165–167° C.

$^1$H-NMR: (Me$_2$SO-d$_6$) δ 7.62 (s, 1H, purine H-8), 6.09 (m, 1H 0.5 CH=CH), 5.90–5.82 (m overlapping br s at 5.86, 3H, 0.5 CH=CH, NH$_2$), 5.39 (m, 1H, NCH) 4.72 (t, J=5.0 Hz, 1H, OH) 4.09 and 3.64 (br, m, 8H, 4CH$_2$ on morpholine ring), 3.42 (m, 2H, OCH$_2$), 2.84 (br m, 1H, CH), 2.65–2.54 and 1.59–1.47 (m, 2H, CH$_2$).

Anal. Calcd. for C$_{15}$H$_{20}$N$_6$O$_2$: C, 56.95; H, 6.37; N, 26.57.

Found: C, 57.03; H, 6.41; N, 26.48.

EXAMPLE 20

(±)-cis-4-(2-Amino-6-benzylamino-9H-purin-9-yl)-2-cyclopentene-1-methanol

A solution of (±)-cis-4-(-2-Amino-6-chloro-9H)-purin-9-yl)-2-cyclopentene-1-methanol (0.531 g, 2.00 mmol) from Example 4, benzylamine (0.214 g, 2.00 mmol) and triethylamine (1.717 g, 17 mmol) in the ethanol (6 mL) was stirred at reflux for 4 hours. The reaction mixture was allowed to cool to room temperature before the addition of 2 mL of 1.0 N NaOH. Concentration of the mixture afforded the crude product which was eluted from a silica gel column with 5% methanol-chloroform. Crystallization of such a sample from ethanol-water yielded a white powder (0.386 g, 57%); m.p. 174–176° C.

$^1$H-NMR: (Me$_2$SO-d$_6$) δ 7.80–7.65 (br s, 1H, NH), 7.60 (s, 1H, purine H-8), 6.08 (m, 1H 0.5 CH=CH), 5.86–5.82 (m overlapping br s, 3H 0.5 CH=CH, NH$_2$), 5.35 (br m, 1H, NCH), 4.73 (t, J=4.9 Hz, overlapping br s at 4.65, 3H, OH, NCH$_2$) 3.43 (m, 2H, 0CH$_2$), 85–2.81 (br m, 1H, CH), 2.65–2.54 and 1.63–1.50 (m, 2H, CH$_2$).

Anal. Calcd. for C$_{18}$H$_{20}$N$_6$O: C, 64.27; H, 5.99; N, 24.98.

Found: C, 64.35; H, 6.02; N, 24.92.

EXAMPLE 21

(±)-cis-4-(2-Amino-6-(2-methoxyethoxy-9H-purin-9-yl)-2-cyclopentene-1-methanol

A flask was charged with sodium hydride (60% oil dispersion, 298 mg, 7.45 mmol) which was then washed with hexanes before the addition of methoxyethanol (15 mL), (±)-cis-4-(2-Amino-6-chloro-9H-purin-9-yl)-2-cyclopentene-1-methanol (0.531 g, 2 mmol) from Example 4 was added and the solution was stirred at 100° C. for 1 hour and then neutralized by the addition of 1.0 N HCl. Concentration of the solution afforded the crude product which was purified by elution from a silica gel column with 5% methanol-chloroform (416 mg, 68%). Crystallization from ethanol gave an off-white powder, m.p. 121–123° C.

$^1$H-NMR: (Me$_2$SO-d$_6$) δ 7.78 (s, 1H, purine H8), 6.39 (br s, 2H, NH$_2$), 6.14 and 5.90 (m, 2H, CH=CH), 5.44 (br m, 1H, NCH), 4.72 (t, J=4.6 Hz, 1H, OH) 4.72 and 3.69 (m, 4H, OCH$_2$CH$_2$O), 3.45 (m, 2H, OCH$_2$), 3.31 (s, overlapping with H$_2$O, OCH$_3$), 2.88 (br m, 1H, CH), 2.67–2 60 and 1.65–1.58 (m, 2H, CH$_2$).

Anal. Calcd. for C$_{14}$H$_{19}$N$_5$O$_3$: C, 55.07; H, 6.27; N, 22.94.

Found: C 55.18; H, 6.33; N, 22.95.

EXAMPLE 22

(±)-cis-4-(2-Amino-6-propylamino-9H-purin-9-yl)-2-cyclopentene-1-methanol

A solution of (±)-cis-4-(-2-Amino-6-chloro-9H-purin-9-yl)-2-cyclopentene-1-methanol (0.531 g, 2.00 mmol) from Example 4 and propylamine (1.12 g, 18.19 mmol) in 8 mL of ethanol was stirred at reflux for 2 hours. The solution was allowed to cool to room temperature before the addition of 2 mL of 1.0 N NaOH. Concentration of the solution afforded the crude product which was purified by elution from a silica gel column with 5% methanolchloroform (0.46 g, 80%). Crystallization of such a sample from ethanol-ethyl acetate yielded a white powder, m.p. 138–140° C.

$^1$H-NMR: (Me$_2$SO-d$_6$) δ 7.57 (s, 1H, purine H-8); 7.20–7.05 (br s, 1H, NH); 6.11–6.06 and 5.86–5.82 (both m, 2H, CH=CH); 5.78–5.70 (br s, 2H, NH$_2$); 5.39 (m,1H, NCH); 4.73 (t, J=5.3, 1H, OH); CH); 2.65–2.54 (m, 1H 0.5 cyclopentyl CH$_2$); 1.62–1.58 (m, 3H, 0.5 cyclopentyl CH$_2$, CH$_2$); 0.86 (t, J=7.4 Hz, 3H, CH$_3$).

Anal. Calcd. for C$_{14}$H$_{20}$N$_6$O: C, 58.32; H, 6.99; N, 29.15.

Found: C, 58.38; H, 7,02; N, 29.10.

EXAMPLE 23

(±)-cis-4-(2-Amino-6-anilino-9H-purin-9-yl)-2-cyclopentene-1-methanol

A solution of (±)-cis-4-(2-Amino-6-chloro-9H-purin-9-yl)-2-cyclopentene-1-methanol (0.550 g, 2.07 mmol) from Example 4 and aniline (0.965 g, 10.35 mmol) in 10 mL of methoxyethanol was stirred at 95° C. for 1 hour. The reaction mixture was allowed to cool to room temperature before the addition of 2.05 mL of 1 N NaOH. Concentration of the solution afforded the crude product which was purified by elution from a silica gel column with 5% methanolchloroform (0.60 g, 90%). Crystallization of such a sample from methanol-acetonitrile gave an off-white powder m.p. 177–179° C.

$^1$H-NMR: (Me$_2$SO-d$_6$ $_4$ 9.32 (s, 1H, NH); 8.00 (d, J=7.8 Hz, 2H, C$_6$H$_5$); 7.74 (s, 1H, purine H-8); 7.25 (m, 2H, C6H5); 6.94 (m, 1H, C$_6$H$_5$); 6.18–6.05 (br m, 3H, NH$_2$, $_{0.5}$ CH=CH); 5.88 (m, 1H, 0.5 CH=CH); 5.50–5.35 (br m, 1H, NCH); 4.74 (m, 1H, OH); 3.45 (m, 2H, CH$_2$O); 2.97–2.80 (br m, 1H, CH); 2.65 and 1.61 (2m, 2H, CH$_2$).

Anal. Calcd. for C$_{17}$H$_{18}$N$_6$O: C, 63.34; H, 5.63; N, 26.07.

Found: C, 63.26; H, 5.67; N, 26.01.

EXAMPLE 24

(±)-cis-4-(2-Amino-6-methylamino-9H-purin-9-yl)-2-cyclopentene-1-methanol (±)-cis-4-(2-Amino-6-chloro-9H-purin-9-yl)-2-cyclopentene-1-methanol (0.400 g, 1.5 mmol) from Example 4 and methylamine (40% aqueous solution, 25 mL) were stirred at 60° C. for 0.5 hours. The solution was allowed to cool to room temperature before the addition of 1.5 mL of 1.5 N NaOH. Evaporation left the crude product which was purified by elution from a silica gel column with 5% methanolchloroform. The resulting solid was slurried in acetonitrile to yield a pale yellow powder (0.274 g, 70%); m.p. 221-223° C.

$^1$H-NMR: (Me$_2$SO-d$_6$) d 7.57 (s, 1H, purine H-8); 7.12 (br s, 1H, NH); 6.11-6.06 (m, 1H, 0.5 CH=CH); 5.87-5.80 (m, overlapping br s at 5.80, total 3H 0.5 CH=CH, NH$_2$); 5.40-5.33 (m, 1H, CHN); 4.76-4.70 (m, 1H, OH); 3.43 (m, 2H, CH$_2$O); 2.95-2.77 (br s, 4H, CH$_3$, CH); 2.65-2.54 and 1.62-1.50 (both m, 2H, CH$_2$).

Anal. Calcd. for C$_{12}$H$_{16}$N$_6$O: C, 55.37; H, 6.20; N, 32.29.

Found: C, 55.28; H, 6.24; N, 32.19.

EXAMPLE 25

(±)-cis-4-(2-Amino-6-dimethylamino-9H-purin-9-yl)-2-cyclopentene-1-methanol (±)-cis-4-(2-Amino-6-chloro-9H-purin-9-yl)-2-cyclopentene-1-methanol (0.400 g, 1.5 mmol) from Example 4 and dimethylamine (25% aqueous solution, 20 mL) was stirred at 80° C. for 0.5 hours. The reaction mixture was allowed to cool to room temperature before the addition of 1.5 mL of 1 N NaOH. Concentration of the solution afforded the crude product which was purified by elution from a silica gel column with 5% methanol-chloroform (0.310 g, 75%). Crystallization of such a sample from ethanol-water gave an off-white powder m.p. 173-174° C.:

$^1$H-NMR: (Me$_2$SO-d$_6$) δ 7.60 (s, 1H, purine H-8); 6.10 and 5.84 (both m, 2H, CH=CH); 5.78 (s, 2H, NH$_2$); 5.39 (m, 1H, CHN); 4.72 (m, 1H, OH); 3.42 (m, OCH$_2$ overlapping with H$_2$O, NMe$_2$); 3.33 and 3.31 (both s, N (CH$_3$)$_2$ overlapping with H$_2$O, OCH$_2$); 2.90-2.78 (m, 1H, CH); 2.65-2.53 and 1.59-1.47 (both m, 2H, CH$_2$).

Anal Calcd. for C$_{13}$H$_{18}$N$_6$O: C, 56.92; H, 6.61; N, 30.63.

Found: C, 56.93; H, 6.64; N, 30.56.

EXAMPLE 26

(±)-cis-4-(2-Amino-6-propoxy-9H-purin-9-yl)-2-cyclopentene-1-methanol

A flask was charged with sodium hydride (60% oil dispersion 158 m8, 3 mMol) which was then washed with hexanes before the addition of n-propanol (25 mL). (±)-cis-4-(2-Amino-6-chloro-9H-purin-9-yl)-2-cyclopentene-1-methanol from Example 4 (400 mg, 1.5 mmol) was added and the solution was stirred at 80° C. for 2 hours and the neutralized by the addition of 1.0 N HC1. Concentration of the solution afforded the crude product which was purified by elution from a silica gel column with 2% methanol-chloroform (350 mg, 81%). Crystallization of such a sample from ethanol-water gave an off-white powder, m.p. 97-99° C.

$^1$H-NMR: (Me$_2$SO-d$_6$) 4 7.74 (s, 1H, purine, H-8); 6.34 (s, 2H, NH$_2$); 6.11 and 5.85 (both m, 2H, CH=CH); 5 41 (m, 1H, CHN); 4.71 (m, 1H, OH); 4.34 (t, J=6.8, 2H, OCH$_2$); 3.44 (m, 2H, CH$_2$ OH); 2.85 (m, 1H, CH); 2.60 (m, 1H, 0.5 CH$_2$); 1.74 (m, 2H, CH$_2$CH$_3$); 1.61 (m, 1H, 0.5 CH$_2$); 0.95 (t,J=7,4, 3H, CH$_3$).

Anal. Calcd. for C$_{14}$H$_{19}$N$_5$O$_2$·0.35H$_2$O: C, 56.88; H, 6.72; N, 23.69.

Found: C, 57.00; H, 6.78; N, 23.61. C, 56.93; H, 6.81; N, 23.59.

EXAMPLE 27

(±)-cis-4-(2-Amino-6-((2-hydroxyethyl)amino)-9H-purin-9-yl)-2-cyclopentene-1-methanol A flask charged with (±)-cis-4-(2-Amino-6-chloro-9H-purin-9-yl)-2-cyclopentene-1-methanol (0.53 g, 2.00 mmol) from Example 4, triethylamine (0.92 g, 9.10 mmol), ethanolamine (0.172 g, 2.82 mmol) and methoxyethanol (6 mL) was stirred at reflux for 2 hours. The solution was allowed to cool to room temperature before the addition of 2 mL of 1.0 N NaOH. Concentration of the solution left the crude product which was purified by elution from a silica gel column with 10% methanol chloroform (0.430 g, 74%). Crystallization of such a sample from ethanol-water gave a white powder, m.p. 150-152° C.

$^1$H-NMR: (Me$_2$SO-d$_6$) 4 7.57 (s, 1H, purine H-8), 7.00-6.87 (br s, 1H, NH), 6.11-6.06 (m, 1H, 0.5 CH=CH), 5.87-5.80 (m, overlapping br s, 3H 0.5 CH=CH, NH$_2$), 5.37 (m, 1H, CHN), 4.72 (two t, 2H, 2OH) 3.53-3.40 (m, 6H, 2 OCH$_2$), 2.87-2.80 (br m, 1H, CH) 2.65-2.54 and 1.62-1.50 (2m, 2H, OH$_2$).

Anal. Calcd. for C$_{13}$H$_{18}$N$_6$O$_2$: C, 53.78; H, 6.25; N, 28.95.

Found: C, 53.89; H, 6.33; N, 28.90.

EXAMPLE 28

(±)-cis-4-(2-Amino-6-(2-cyclopenten-1-yl amino)-9H-purin-9-yl)-2-cyclopentene-1-methanol A solution of (±)-cis-4-(2-Amino-6-chloro-9H-purin-9-yl)-2-cyclopentene-1-methanol hydrate (0.53 g, 1.87 mmol) from Example 4, triethylamine (2.00 g, 20 mmol) and 3-amino cyclopentene hydrochloride (463 mg, 3.87 mmol) in 10 mL of ethanol was stirred at reflux for 17 hours. The solution was allowed to cool to room temperature before the addition of 2 mL of 1.0 N NaOH. Concentration of the solution afforded the crude product which was purified by elution from a silica gel column using 5% methanol in chloroform (0.30 g, 48.0%). Crystallization of such a sample from ethanol-acetonitrile gave an off-white powder, m.p. 143-146° C.

$^1$H-NMR: (Me$_2$SO-d$_6$) δ 7.58 (s, 1H, purine H8); 6.97 (br d J=12 Hz, 1H, NH); 6.10 (m, 1H, =CH); 5.89-5.72 (m overlapping br s at 5.86, 5H, 3=CH,NH2); 5.37 (m overlapping br m at 5.2; 4.73 (unresolved t, 1H, OH); 3.42 (m, 2H, 0CH$_2$); 2.84 (br m, 1H, CH) 2.66-2.14 (m, overlapping DMSO, 3×0.5 CH$_2$); 1.80-1.48 (m, 2H, 2×0.5 CH$_2$).

Anal. Calcd. for C$_{16}$H$_{20}$N$_6$O: C, 61.52; H, 6.45; N, 26.9.

Found: C, 61.62; H, 6.47; N, 26.88.

EXAMPLE 29

(±)-cis-4-[2-Amino-6-[[cis-3-(hydroxymethyl)-1-cyclopentyl]amino]-9H-purin-9-yl]-2-cyclopentene-1-methanol A solution of (±)-cis-4-(2-Amino-6-chloro-9H-purin-9-yl)-2-cyclopentene-1-methanol (530 mg, 2.00 mmol) from Example 4, 3-aminocyclopentyl-1-methanol (276 mg, 24 mmol), triethylamine (1.12 g, 10.98 mmol), and ethanol (20 mL) was stirred at reflux for 5 hours. An additional amount of triethylamine (1.17 g) was then added and the solution was refluxed for 8 additional hours. The solution was allowed to cool to room temperature and 2 mL of 1 N NaOH was added. The solution was concentrated and the residues were placed on silica gel column which was eluted with 10% methanol-chloroform (0.36 g, 52%). Recrystallization of such a sample from ethanolacetonitrile gave title compound as white powder, m.p. 177–180° C.

$^1$H-NMR: (Me$_2$SO-d$_6$-) $\delta$ 7.59 (s, 1H purine H.8), 7.06 (br s, 1H, NH) 6.12 and 5.87 (m, 2H, HC=CH) 5.78 (br s, 2H, NH$_2$), 5.38 (br m, 1H, NCH, cyclopentene) 4.76 (t, J=5.3, OH cyclopentene), 4.59 (t, J=6.6, 1H, OH) 4.47 (br m, 1H, NCH), 3.44 (m, 2H, OCH$_2$ cyclopentene), 3.35 (m, overlapping with H$_2$O, OCH$_2$ cyclopentane) 2.87 (br m, 1H, CH cyclopentene), 2.58 (m, 1H 0.5 CH$_2$ cyclopentene), 2.05, 1.85, 1.68–1.43 and 1.25 (br m, total 8H, 3 CH$_2$ cyclopentene, 1 CH cyclopentane, 0.52 CH$_2$ cyclopentene).

Anal. Calcd. C$_{17}$H$_{24}$N$_6$O$_2$: C, 59.29; M, 7.02; N, 24.40.
Found: C, 59.12; H, 6.97; N, 24.32.

EXAMPLE 30

($\pm$)-cis-4-[2-Amino-6-((R)-sec-butoxy)-9H-purin-9-yl]-2-cyclopentene-1-methanol A flask was charged with sodium hydride (60% oil dispersion, 300 mg, 7.5 mmol) which was washed with hexanes before the addition of ($\pm$)-cis-4-(2-amino-6-chloro-9H--purin-9-yl)-2-cyclopentene-1-methanol from Example 4 (800 mg, 3 mmol) in ~10 mL of R-(-)-2-butanol. The solution was stirred at room temperature for 3 hours then at 60° C. (oil bath) for 1 hour. The solution was allowed to cool to room temperature before neutralization with 1 H HCl. The solution was concentrated and the residue chromatographed on silica gel. Title compound was eluted with 5% methanol-chloroform (0.81 g, 89%). Crystallization of such a sample from ethanol-acetonitrile yielded an off-white powder, m.p. 159–161° C.

$^1$H-NMR: (Me$_2$SO-d$_6$) $\delta$ 7.72 (s, 1H, purine H.8), 6.30 (br s, 2H, NH$_2$), 6.10 and 5.86 (m, 2H, HC=CH), 5.44–5.28 (m, 2H, NCH, OCH), 4.71 (t, J=5.0, 1, OH), 3.42 (m, 2, OCH$_2$), 2.85 (m, 1, CH), 2.60 (m1, 0.5 CH$_2$ cyclopentene), 1.61 (m, 3H 0.5 CH$_2$ cyclopentene, CH$_2$) 1.27 (d, J=6.0, 3H, CHCH$_3$), 0.89 (t, J=7.4,3H, CH$_3$).

Anal. Calcd. C$_{15}$H$_{21}$N$_5$O$_2$: C, 59.39; H, 6.98; N, 23.09.
Found: C, 59.28; H, 7.01; N, 23.02.

EXAMPLE 31

($\pm$)-cis-4-(2-Amino-6-butylamino-9H-purine-9-yl)-2-cyclopentene-1-methanol

A solution of ($\pm$)-cis-4-(2-amino-6-chloro-9H-purin-9-yl)-2-cyclopentene-1-methanol from Example 4 (0.408 g, 1.5 mmol): butylamine (0.549 g, 7.5 mmol, 5 eqv.) and ethanol (10 mL) was stirred at reflux for 3 hours. The solution was allowed to cool to room temperature before the addition of 1.5 mL of 1.0 N NaOH. The solution was concentrated and the residues were purified by elution from a silica gel column with 5% methanol-chloroform (0.440 g, 97%). The title compound was dissolved in hot acetonitrile then cooled to produce a white powder, m.p. 116–118° C.

$^1$H-NMR: (Me$_2$SO.d$_6$) $\delta$ 7.57 (s, 1H, purine H.8) 7.12 (br m, 1H, NH), 6.09 and 5.85 (m, 2H, HC=CH), 5.75 (br s, 2H, NH$_2$) 5.36 (br m, 1H, NCH), 4.74 (t, J=5.3, 1H, OH), 3.42 (m, 4H, OCH$_2$, NCH$_2$), 2.84 (br m, 1H, CH), 2.58 (m, 1H, 0.5 CH$_2$ cyclopentene), 1.52 (m, 3H 0.5 CH$_2$ cyclopentene, CH$_2$ butyl), 1.30 (m, 2H, CH$_2$ butyl), 0.87 (t, J=7.2, 3H, CH$_3$).

Anal. Calcd. C$_{15}$H$_{22}$N$_6$O: C, 59.58; H, 7.34; N, 27.80.
Found: C, 59.44; H, 7.38; N, 27.79.

EXAMPLE 32

($\pm$) cis-4-(2-Amino-6-((S)-sec-butoxy)-9H-purin-9-yl)-2-cyclopentene-1-methanol A flask was charged with sodium hydride (60% oil dispersion, 300 mg, 7.5 mmol) which was washed with hexanes before the addition of ($\pm$)-cis-4-(2-Amino-6-chloro-9H-purin-9-yl)-2-cyclopentene-1-methanol from Example 4 (800 mg, 3 mmol) in S-(t)-2-butanol (10 mL). The solution was stirred at room temperature for 6 hours before neutralization with 1N HCl. The solution was concentrated and the residue was placed on a silica gel column. Title compound was eluted with 5% methanol-chloroform (0.29 g, 32%). Crystallization of such a sample from ethanol: acetonitrile yielded an off-white powder, m.p. 159–162° C.

$^1$H-NMR (Me$_2$SO-d$_6$) $\delta$ 7.72 (s, 1H, purine H.8), 6.30 (br s, 2H, NH$_2$) 6.10 and 5.86 (m, 2H, HC=CH), 5.44–5.28 (m, 2H, NCH, OCH) 4.71 (t, J=5.0, 1H, OH), 3.42 (m, 2H, OCH$_2$), 2.85 (m, 1H, CH), 2.60 (m, 1H, 0.5 CH$_2$ cyclopentene), 1.61 (m, 3H, 0.5 CH$_2$ cyclopentene, CH$_2$), 1.27 (d, J=6.0, 3H, CH, CH$_3$), 0.89 (t, J=7.4, 3H, CH$_3$).

Anal. Calcd. C$_{15}$H$_{21}$N$_5$O$_2$.0.25 H$_2$O: C, 58.52; H, 7.04; N, 22.75.
Found: C, 58.59; H, 6.94; N, 22.79.

EXAMPLE 33

($\pm$)-cis-4-(2-Amino-6-[(6-hydroxyhexyl)thio]-9H-purin-9-yl)-2-cyclopentene-1-methanol To a solution of ($\pm$)-cis-2-amino-1,9-dihydro-9-[(4-hydroxymethyl)-2-cyclopentenyl]-6H-purin-6-thione-HCl, from Example 8 (0.50 g, 1.45 mmol) in 1 N NaOH (2.9 mL) was added 6-bromo-1-hexanol (0.321 g, 1.77 mmol) in dioxane (1 mL). The solution was stirred at room temperature under nitrogen for 5 hours during which time additional 6-bromo-1-hexanol (0.096 g, 0.53 mMol) and 1 N NaOH (0.53 ml) were added. The solution was evaporated to remove dioxane and the aqueous layer was extracted with 3×25 ml chloroform. Combined chloroform extracts were dried (MgSO$_4$). Solvent was evaporated and the residual oil was chromatographed on silica gel. The title compound was eluted with 10% methanol-chloroform; white solid was formed after crystallization from acetonitrile (0.469 g, 89%), m.p 129–130° C.

$^1$H-NMR (DMSO-d$_6$) $\delta$ 7.84 (s, 1, H-8), 6.46 (br s, 2, NH$_2$), 6.15 and 5.90 (2m, 2, CH=CH), 5.45 (br m, 1, CH-N), 4.73 (t, J=5.4, i, OH) 4.36 {t, J=5.2, 1, (CH$_2$)$_6$-OH), 3.5o-3.20 (all m, overlapping H$_2$O, 2CH$_2$-O CH$_2$S), 2.90 (br m, 1, CH), 2.70–2.55 (m, 1, 0.5 CH$_2$), 1.70–1.50 (m, 3, S-CH$_2$-CH$_2$) and 0.5 CH$_2$), 1.50–1.20 (br m, 6, 3CH$_2$S).

Anal Calcd. C$_{17}$H$_{25}$N$_5$O$_2$S: C, 56.18; H, 6.93; N, 19.27; S, 8.82.
Found: C, 56.09; H, 6.93; N, 19.22; S, 8.90.

EXAMPLE 34

($\pm$)-cis-4-(2-Amino-6-(isopropylamino)-9H-purin-1-yl)-2-cyclopenten-1-methanol ($\pm$)-cis-4-12-Amino-6-chloro-9H-purin-9-yl)-2-cyclopentene-1-methanol from Example 4 (0.545 g, 2 mmol), isopropylamine (2.36 g, 40 mmol) and methanol (15 mL) were placed in a Parr bomb and heated at 65–70° C. for 12 hours. 1 N NaOH (2 mL) was added and the solution evaporated to dryness. The residue was dried by evaporation of ethanol and chromatographed on silica gel. The title compound was eluted with 10% methanol-chloroform; white solid was formed after crystallization from acetonitrile (0.463 g, 80%), m.p. 153–155° C.;

$^1$H-NMR (DMSO-d$_6$) δ 7.60 (s, 1, H8), 6.90 (br m, 1, NH), 6.10 and 5.85 (2m, 2, CH=CH), 5.70 (br s, 2, NH$_2$), 5.40 (br m 1, CH-N), 4.75 (t, J=5, O, 1, OH), 4.60–4.40 (br m 1, CH—NH), 3.45 (m, 2, CH$_2$-O) 2.85 (br m, 1, CH), 2.65–2.55 (m, 1 0.5 0H$_2$) 1.65–1.55 (m, 1, 0.5 CH$_2$), 1.17 (d, J=6.5, 6, 2CH$_3$).

Anal. Calcd. C$_{14}$H$_{20}$H$_6$O: C, 58.32; H, 6.99; N, 29.15. Found: C, 58.42; H, 7.00; N, 29.23.

EXAMPLE 35

(±)-cis-4-(2-Amino-6-(butylthio)-9H-purin-9-yl]-2-cyclopenten-1-methanol

To a solution of (±)-cis-2-amino-1,9-dihydro-9-[(4-hydroxymethyl)-2-cyclopentenyl]-6H--purin-6-thione from Example 8 (0.50 g, 1.89 mmol) in 1 N NaOH (1.89 mL) was added butyliodide (0.348 g, 1.89 mmol), in dioxane (5 mL). The solution was stirred for 5 hours under nitrogen at 25° C. and extracted with CHCl$_3$ (3×100 mL). The combined chloroform extracts were dried (MgSO4), solvent evaporated and the residual oil crystallised from acetonitrile to give title compound as yellow powder (0.491g, 81%), m.p. 120–123° C.

$^1$H-NMR: (DMSO-d$_6$) δ 7.82 (s, 1H-8), 6.43 (br s, 2, NH$_2$), 6.15 and 5.85 (2m, 2, CH=CH), 5.40 (m, 1, CH—N), 4.70 (m, 1, OH), 3.43 (m, 2, CH$_2$-O), 3.25 (t, J=7.4, overlapping H$_2$O, S—CH$_2$), 2.85 (br m, 1, CH), 2.70–2.55 (m, 1, 0.5 CH$_2$), 1.70–1.30 (m, 5 —CH$_2$—CH$_2$—+1/2 CH$_2$), 0.89 (t, J=7.2, 3, CH$_3$).

Anal. Calcd. C$_{15}$H$_{21}$N$_5$OS: C, 56.40; H, 6.62; N, 21.93; S, 10.04.

Found: C, 56.31; H, 6.64: N, 21.89; S, 10.02.

EXAMPLE 36

(±)-cis-4-(2-Amino-6-(isobutylthio)-9H-purin-9-yl)-2-cyclopentene-1-methanol

To a solution of (±)-cis-2-amino-1,9-dihydro-9-[(4-hydroxymethyl)-2-cyclopenten-1-yl]-6H-purine-6-thione-HCl from Example 8 (0.50 g, 1.45 mmol), in 1 N NaOH (2.9 ml) was added 1-iodo-2-methylpropane (0.326 g, 1.77 mmol) in dioxane (1 mL). The reaction was stirred at room temperature under nitrogen for 24 hours during which time additional 1-iodo-2-methyl propane (0.130 g, 0.71 mmol) and 1 N NaOH (0.71 ml) were added. The solution was then evaporated to remove dioxane and the aqueous layer extracted with 3×25 ml chloroform. The combined chloroform extracts were dried (MgSO$_4$), solvent evaporated and the residual oil chromatographed on silica gel. The title compound was eluted with 10% methanol-chloroform; white powder was formed after crystallization from acetonitrile (0.345 g, 75%), m.p. 127–129° C.

$^1$H-NMR: (DMSO-d$_6$) δ 7.82 (s, 1, H-8), 6.44 (br s, 2, NH$_2$), 6.15 and 5.85 (2m, 2, CH=CH), 5.45 (br m, 1, CH-N), 4.71 (m, 1, OH), 3.45 (m, 2, CH$_2$-0), 3.18 (d, J=6.6, 2, S-CH$_2$), 2.85 (br m, 1, CH), 2.70–2.50 (m, overlapping solvent, 0.5 CH$_2$), 2.0–1.80 (m, 1, Me$_2$CH), 1.70–1.50 (m, 1, 0.5 CH$_2$), 0.983 (d, J=6.6, 6, 2CH$_3$).

Anal. Calcd. C$_{15}$H$_{21}$N$_5$OS: C, 56.40; H, 6.62; N, 21.93; S, 10.04.

Found; C, 56.48; H, 6.61; N, 21.93; S, 10.10.

EXAMPLE 37

(±)-cis-4-(2-Amino-6-(cyclopentylthio)-9H-purin-9-yl)-2-cyclopentene-1-methanol

To a solution of (±)-cis-2-amino-1,9-dihydro-9-[(4-hydroxymethyl)-2-cyclopentene-1-yl)-6H-purin-6-thione from Example 8 (0.50 g, 1.89 mmol) in 1 N NaOH (1.89 ml) was added cyclopentylbromide (0.282 g, 1.89 mmol) in dioxane (1 mL). The solution was stirred under nitrogen at room temperature for 24 hours during which time additional cyclopentyl bromide (0.846 g, 5.67 mmol) and 1 N NaOH (5.67 ml) were added. The solution was evaporated to remove dioxane and the aqueous layer extracted with 3×50 ml of chloroform. The combined extracts were dried (MgSO$_4$), solvent evaporated and the residual oil chromatographed on silica gel. The title compound was eluted with 10% methanol-chloroform and solidified in acetonitrile to give title compound as yellow powder (0.310 g, 50%), m.p. 167–169° C.

$^1$H-NMR: (DMSO-d$_6$) δ 7.83 (s, 1, H-8), 6.43 (br s, 2, NH$_2$), 6.13 and 5.87 (2M, 2, CH=CH), 5.42 (br m, 1, CH—N), 4.72 (t, J=5.3, 1, OH), 4.30 (m, 1, S—CH), 3.44 (m, 2, CH$_2$-O), 2.85 (br m, 1, CH), 2.70–2.55 (m, 1, 0.5 CH$_2$), 2.30–2.15 (br m, 2, 2CH), 1.80–1.50 (m, 7, 2CH$_2$ plus 3/2 CH$_2$).

Anal. Calcd. C$_{16}$H$_{21}$N$_5$OS: C, 57.98; H, 6.39; N, 21.13; S, 9.67.

Found: C, 57.82; H, 6.42; N, 21.10; S, 9.57.

EXAMPLE 38

(±)-cis-4-(2-Amino-6-[(cyclopropylmethyl)thio]-9H-purin-9-yl)-2-cyclopentene-1-methanol To a solution of (±)-cis-2-amino-1,9-dihydro-9-[(4-hydroxymethyl)-2-cyclopentenyl]-6H-purin-6-thione-HCl from Example 4 (0.50 g, 1.45 mmol), 1 N NaOH (2.9 ml) was added bromomethyl cyclopropane (0.239 g, 1.77 mmol) in dioxane (1 ml). The solution stirred under nitrogen at room temperature for 2 hours and was then extracted with 3×50 mL chloroform. The combined chloroform extracts were dried (MgSO$_4$), solvent evaporated and residual oil chromatographed on silica gel. The title compound was eluted with 10% methanolchloroform; white solid was formed after crystallization from acetonitrile (0.350 g, 76%), m.p. 125–127° C.

$^1$H-NMR: (DMSO-d$_6$) δ 7.82 (s, 1, H-8), 6.44 (br s, 2, NH$_2$), 6.10 and 5.85 (2m, 2, CH=CH), 5.40 (br m, 1, CH—N), 4.71 (m, 1, OH), 3.43 (m, 2, CH$_2$-0), 3.26 (d, J=12.1, 2, S—CH$_2$), 2.85 (br m, 1, CH), 2.70–2.50 (m, overlapping solvent, 0.5 CH$_2$), 1.70–1.50 (m, 1, 0.5 CH$_2$), 1.20.1.0 (m, 1, CH cyclopropyl), 0.55 and 0.35 (both m, 4, cyclopropyl CH$_2$).

Anal. Calcd. C$_{15}$H$_{19}$N$_5$OS; C, 56.76; H, 6.03; N, 22.07; S, 10.10.

Found: C, 56.65; H, 6.05; N, 22.01; S, 10.19.

EXAMPLE 39

(±)-cis-4-(2-Amino-6-((6-hydroxyhexyl)amino)9H-purin-9-yl-2-cyclopentene-1-methanol A solution of (±)-(cis)-4-(2-amino-6-chloro-9H-purin-9-yl)-2-cyclopentene-1-methanol from Example 4 (0.544 g 2 mmol), triethylamine (0.607 g, 6 mmol) and 6-amino-1-hexanol (0.234 g, 2 mmol) in ethanol (5 mL) was refluxed under nitrogen for 32 hours. During this time additional 6-amino-1-hexanol (0.117 g, 1 mmol)

was added. 1 N NaOH (2 mL) was then added and the solution allowed to stir for 30 minutes. The solution was concentrated under vacuum, and the residual oil was dried by evaporation of ethanol and chromatographed on silica gel. Title compound was eluted with 7% methanol-chloroform; white powder after crystallization from acetonitrile (0.473 g, 68%), m.p. 120-121° C.

$^1$H-NMR: (DMSO-d$_6$) δ 7.57 (s, 1, H-8), 7.10 (br s, 1, NH), 6.10 and 5.85 (2m, 2, CH=CH), 5.74 (br s, 2, NH$_2$), 5.40 (m, 1, CH—N), 4.73 (t, J=5.3, 1, OH), 4.31 (t, J=5.2, (CH$_2$)6-OH), 3.50-3.30 (all m, overlapping H$_2$O, 2, CH$_2$-O and CH$_2$-N), 2.85 (br m, 1, CH), 2.70-2.50 (m, overlapping solvent, 0.5 CH$_2$), 1.70-1.20 (all m, 9, 4 CH$_2$ and 0.5 CH$_2$).

Anal. Calcd. for C$_{17}$H$_{26}$N$_6$O$_2$: C, 58.94; H, 7.56; N, 24.26.

Found: C, 58.85; H, 7.60; N, 25.21.

EXAMPLE 40

(±)-cis-4-(2-Amino-6-l3-butenylthio)-9H-purin-9-yl)-methanol

To a solution of (±)-cis-2-amino-1,9-dihydro-9[(4-hydroxymethyl)-2-cyclopentene-1-yl]-6H--purin-6-thione-HCl from Example 8 (0.50 g, 1.45 mmol) in 1 N NaOH (2.9 ml) was added 4-bromo-1-butene (0.196 g, 1.45 mmol) in dioxane 11 ml). The solution was allowed to stir at room temperature for 5 hours during which time an additional 4-bromo-1-butene (0.196 g, 1.45 mmol) and 1 N NaOH (1.45 ml) were added. The solution was then evaporated to remove dioxane and aqueous layer extracted with chloroform (3×25 ml). The combined chloroform extracts were dried (MgSO$_4$), solvent evaporated and residual oil chromatographed on silica gel. The title compound was eluted with 7% methanol-chloroform; foamed from ethanol under vacuum (0.410 g, 85%).

$^1$H-NMR: (DMSO-d$_6$) δ 7.82 (s, 1, H-8), 6.45 (br s, 2, NH$_2$), 6.10 and 5.85 (2m, overlapping 6.0-5.75, m, total 3, CH=CH and CH=CH$_2$), 5.40 (br m, 1, CH—N), 5.20-5.0 (m, 2, CH=CH$_2$), 4.71 (t, J=5.3, 1,OH), 3.50-3.25 (2m, overlapping H$_{20}$, CH$_2$Y-S, CH$_{2-0}$), 2.85 (br m, 1, CH), 2.70-2.30 (2m, overlapping solvent, 0.5 CH$_2$ and S-CH$_2$ CH$_2$), 1.70-1.50 (m, 1, 0.5 CH$_2$).

Anal. Calcd. for C$_{15}$H$_{19}$N$_5$OS: 0.25 H$_2$O-0.20 EtOH: C, 55.86; H, 6.30; N, 21.15; S, 9.68

Found: C, 55.97; H, 6.19; N, 20.77; S, 10.02.

EXAMPLE 41

(±)-cis-4-(2-Amino-6-(tert-butylamino)-9H-purin-9-yl)-2-cyclopentene-1-methanol (±)-cis-4-(2-Amino-6-chloro-9H-purin-9-yl)-2-cyclopentene-1-methanol from Example 4 (0.544 g, 2.0 mmol) and tert-butylamine (15 mL) were heated at 80° C. in a Parr bomb for 28 hours. The resulting solution was concentrated and the residual oil was dried by evaporation of ethanol and chromatographed on silica gel. Title compound was eluted with 5% methanol-chloroform; crystallization from acetonitrile gave white powder (0.392 g, 65%), m.p. 161-163° C.

$^1$H-NMR: (DMSO-d$_6$) δ 7.56 (s, 1, H-8), 6.10 (m, overlapping s at 6.03, total 2, =CH and NH), 5.85 (m, overlapping s at 5.78, total 3, =CH and NH$_2$); 5.40 (br m, 1, CH-N); 4.72 (t, J=5.3, 1, OH); 3.40 (m, 2, CH$_2$-O); 2.85 (br m, 1, CH), 2.70-2.50 (m, overlapping solvent, 0.5 CH$_2$), 1.65-1.40 (m, overlapping s at 1.45, total 10, 0.5 CH$_2$ and 3 CH$_3$).

Anal. Calcd. for C$_{15}$H$_{22}$N$_6$O: C, 59.58; H, 7.33; N, 27.79.

Found C, 59.58, H, 7.35; N, 27.86.

EXAMPLE 42

(±)-9-[3-(Hydroxymethyl)-3-cyclopenten-1-yl)guanine

A. (±)-Methyl 4-acetamido-1-cyclopentene-1-carboxylate (±)-cis-Methyl 4-acetamido-2-cyclopentene 1-carboxylate [S. Daluge and R. Vince, *J. Org. Chem.* 1978. 43, 2311](3.90 g, 21.3 mmol) was dissolved in dry methanol (25 mL) and added to a solution of sodium methoxide prepared from sodium (0.98 g, 43 m.equiv.) and dry methanol (150 mL). This solution was stirred at 25° C. for 2.0 hours and then neutralized with 1 N hydrochloric acid. The solution was concentrated to 40 mL and extracted with chloroform (3×75 mL). The chloroform was dried (MgSO$_4$) and evaporated to colourless glass (3.9 g). Chromatography on silica gel with 1-2% methanol-chloroform gave title compound as white crystals (4.33 g, 82%); m.p. 72-74° C [Lit. *Can. J. Chem.* 1985 63, 2787; m.p. 75-76° C. Sublimation of such a sample at 100°/0.2 mm gave white crystals, m.p. 72-74° C.

$^1$H-NMR: (DMSO-d$_6$) δ 8.055 (br d, 1, NH), 6.68 (m, 1, =CH), 4.3 (m, 1, CHN), 3.65 (s, 3, OMe), 2.9-2.7 and 2.4-2.2 (both m, 4, 2CH$_2$), 1.75 (s, 3, MeC=O).

Anal. Calcd. for C$_9$H$_{13}$NO$_3$: 0.1 H$_{20}$; C, 58.43; H, 7.19; N, 7.57.

Found: C, 58.37; H, 7.34; N, 7.34.

B. (±)-4-Acetamido-1-cyclopentene methanol (±)-Methyl-4-acetamido-1-cyclopentene-1-carboxylate (3.66 g, 20.0 mmol) was dried by evaporation of toluene giving a solution with a final volume of 50 mL. This solution was cooled to −70° C. under nitrogen. A solution of diisobutylaluminum hydride in toluene (1.5 M, 42 mL, 63 mmol) was added dropwise over 2 hours. The resulting hazy solution was stirred at −70° C. for an additional 40 minutes. Cold methanol (5 mL) was added dropwise, followed by a solution of sodium potassium tartrate (11.29 g) in water (15 mL) with the temperature maintained at −70° C. The resulting mixture was allowed to stir at 0° C. for several hours, diluted with methanol (150 mL) and filtered. The methanol was evaporated and the residual brown oil (3.44 g) chromatographed on silica gel. Title compound was eluted as pale yellow oil with 5% methanol-chloroform; 1.30 g (42%).

$^1$H-NMR: (DMSO-d$_6$) δ 8.00 (d, 1, NH), 5.45 (m, 1, =CH), 4.71 (t, J=5.5, 1, OH), 4.35-4.2 (m, 1, CH—N), 4.0-3.9 (m, 2, CH$_2$OH), 2.65-2.5 (overlapping DMSO-d5) and 2.2-2.0 (both m, 4, 2CH$_2$), 1.77 (a, 3, CH$_3$CO); EI-MS: M =155.

C. (±)-9-[3-(Hydroxymethyl)-3-cyclopenten-1-yl)guanine (±)-4-Acetamido-1-cyclopentene methanol (1.40 g, 9.02 mmol) was converted by the procedures of Examples 1-4 to (±)-cis-4-(2-amino-6-chloro-9H-purine-9-yl)-1-cyclopentene-1-methanol as a pale yellow solid foam (0.81 g, 42%), after elution from a silica gel column with 5-10% methanol-chloroform; 'H-NMR and mass spectrum confirm structure with 5-10% contamination by (±)-cis-4-(2-amino-6-chloro-9H-purin-9-yl)-1-cyclopentyl methanol. Hydrolysis of such a sample (455 mg, 1.75 mmol) was carried out in dioxane (5 mL)

and 1 N hydrochloric acid (20 mL) at 70° C. for 12 hours. The resulting solution was brought to pH 6 with sodium hydroxide and evaporated to dryness. The residual solids were slurried in methanol and adsorbed on silica gel. Elution with 33% methanol-chloroform gave title compound as a waxy colourless solid. Three crystallizations from water gave white crystals (214 mg, 50%); m.p. 260° dec.

$^1$H-NMR (DMSO-d$_6$) δ 10.54 (s, 1, NHCO), 8.14 (s, 1, purine H-8), 6.44 (s, 2, NH$_2$), 5.70 (s, 1, =CH), 4.97 (m, 1, CH—N), 4.85 (br t, 1, OH), 4.02 (s, 2, CH$_2$OH), 2.9-2.7 (m, 2, CH$_2$), 2.6-2.5 (m, overlapping DMSO-d$_5$, CH$_2$).

Anal. Calcd. for C$_{11}$H$_{13}$N$_5$O$_2$: C, 53.43; H, 5.30; N, 28.32.

Found: C, 53.24; H, 5.33; N, 28.27.

EXAMPLE 43

(±)-cis-4-(2-Amino-6-((2(dimethylamino)ethyl)amino)-9H-purin-9-yl)-2-cyclopentene-1-methanol A flask charged with (±)-(cis)-4-(2-amino-6-chloro-9H--purin-9-yl)-2-cyclopentene-1-methanol from Example 4 (399 mg, 1.5 mmol), N,N-dimethylaminoethylamine (309 mg, 35 mmol) and ethanol (10 mL) was stirred at reflux for 3.5 hours. The solution was cooled to room temperature before the addition of 1.5 mL of 1 N NaOH. The solution was then concentrated and the residues were placed on a silica gel column. The title compound was eluted with 30% methanolchloroform then concentrated to yield a colorless glass. Dilution in methanol (5 mL) and HCl (0.3 mL, 12 N), followed by evaporation produced a pale yellow solid which was slurried in EtOH; (380 mg, 59%); m.p. dec. >185° C.

$^1$H-NMR: (Me$_2$SO-d$_6$) δ 10.4 9.25, 7.67 XXXX br NH+NH$_2$+) 8.06 1s, 1H, purine H-8), 6.18-6.15 and 5.89-5.86 (both m, 2H, HC=CH), 5.45 (br s, 1H, CH-N) 4.20 (br s, 1H, H-1'), 3.90 (br s, 2H, CH$_2$O), 3.53-3.3 (m, 4H, NCH$_2$CH$_2$N), 2.83 and 2.80 (both s, 6H, NMe$_2$), 2.75-2.55 (m, 1H, 0.5 CH$_2$), 1.70-1.50 (m, 1H, 0.5 CH$_2$).

Anal. Calcd. for C$_{15}$H$_{23}$N$_7$0.0, 3 HC1.0, 25 H$_2$0: C, 41.77; H, 6.19; N, 22.73; Cl, 24.66.

Found: C, 41.51, 41.43; H, 5.88,5.90; N, 22.52,22.48; Cl, 24.61.

EXAMPLE 44

(±)-cis-Ethyl 2-(2-Amino-9-(4-(hydroxymethyl)-2-cyclopenten-1-yl)-9H-purin-6-yl)amino]acetate A solution of (±)-(cis-4-(2-amino-6-chloro-9H-purin-9-yl)-2-cyclopentene-1-methanol from Example 4 (400 mg, 1.50 mmol), ethyl glycinate hydrochloride (237 mg, 1.70 mmol), and triethylamine (516 mg, 5.10 mmol) in absolute ethanol (10 mL) was refluxed under nitrogen for 2 days. The ethanol was evaporated and the residue partitioned between saturated aqueous sodium bicarbonate and chloroform. The chloroform was dried (MgSO$_4$), evaporated, and the residue chromatographed on silica gel. Title compound was eluted with 5% methanol-chloroform as a pale yellow glass (240 mg, 48%) which solidified to off-white powder in acetonitrile ether; m.p. 95-97° C.

$^1$H-NMR: (DMSO-d$_6$) δ 7.62 (s, i, purine H-8), 7.48 (br s, 1, NH), 6.10 (m, 1, =CH), 5.84 (m, 3, =CH and NH$_2$), 5.37 (m, 1, CH—N), 4.73 (t, J=5.3, 1, OH), 4.08 (m, 4, OCH$_2$CH$_3$ and NCH$_2$), 3.425 (t, J=5.5, 2, CHOH), 2.85 (m, 1, CH), 2.60 and 1.60 (both m, 1 each, CH$_2$).

Anal. Calcd. for C$_{15}$H$_{20}$N$_6$O$_3$: C, 54.21; H, 6.07, N, 25.29.

Found: C, 54.45; H, 5.93; N, 25.07.

EXAMPLE 45

(±)-cis-4-(2-Amino-6-piperidino-9H-purin-9-yl)-2-cyclopentene-1-methanoldihydrochloride A solution of (±)-(cis)-4-(2-amino-6-chloro-9H--purin-9-yl)-2-cyclopentene-1-methanol from Example 4 (399 mg, 1.50 mmol) and piperidine (298 mg, 3.5 mmol) in absolute ethanol (10 mL) was refluxed under nitrogen for 1 hour. 1 N sodium hydroxide (1.5 mL) was added and the solution evaporated in dryness. The residue was chromatographed on silica gel. The title compound was eluted with 10% methanolchloroform as pale yellow glass (0.30 g). Precipitated as hydrochloride from acetonitrile; white powder (0.30 g, 52%); m.p. dec at 175-180° C.

$^1$H-NMR: (DMSO-d$_6$) δ 7.91 (s, 1, purine H-8), 7.70 (br 3,.2, NH$_2$) 6.2-6.1 and 5.9-5.8 (both m, 2, CH=CH), 5.55-5.4 (br m, 1, CH—N), 5.4-3.8 (br m, NH+, 2CH$_2$N, OH), 3.5-3.35 (m, 1, H-1'), 2.75-2.55 (m, 1, 0.5 CH$_2$), 1.75-1.50 (m, 7, 3CH$_2$ and 0.5 CH$_2$).

Anal. Calcd. for C$_{16}$H$_{22}$N$_6$0.2HCl: C, 49.62; H, 6.25; N, 21.70; Cl, 18.31.

Found: C, 49.54; H, 6.26; N, 21.64; Cl, 18.24.

EXAMPLE 46

(±)-cis-4-[2-Amino-6-((8-Aminooctyl)amino)-9H-purin-9-yl)-2-cyclopentene-1-methanol A solution of (±)-(cis)-4-(2-amino-6-chloro-9H-purin-9-yl)-2-cyclopentene-1-methanol (272 mg, 1.00 mmol) and 1,8-diaminooctane (1.44 g, 10 mmol) in absolute ethanol (15 mL) was refluxed under nitrogen for 1.5 hours. The solution was concentrated, cooled, and the resulting precipitate filtered and crystallised from i-propanol to give title compound as white solid (160 mg, 42%), m.p. 125-127° C.

$^1$H-NMR: DMSO-d$_6$) δ 7.57 (s, 1, purine H-8), 7.10 (br s, 1, NH), 6.10 and 5.85 (both m, 2, CH=CH), 5.74 (br s, 1, NH$_2$), 5.40 (m, 1, CH—N), 4.75 (br m, 1, OH), 3.7-3.0 (br m overlapped by H$_2$0, CH$_2$-O, 2NCH$_2$, NH$_2$), 2.85 (br m, 1, H-4,), 2.7-2.4 (m overlapping d5-DMSO, 0.5 CH$_2$ and CH$_2$ CH$_2$N), 1.55 (m, 3.6, CH$_2$ CH$_2$N and 0.5 CH$_2$), 1.25 (br m, 8, 4CH$_2$).

Anal. Calcd. for C$_{19}$H$_{31}$N$_7$0.0.3H$_2$0: C, 60.23; H, 8.41; N, 25.88.

Found: C, 60.42; H, 8.26; N, 25.78.

EXAMPLE 47

(±)-cis-4-(2-Amino-6-((cyclopropylmethyl)amino)-9((-purin-9-yl)-2-cyclopentene-1-methanol (±)-(cis)-l2-Amino-6-chloro-9H-purin-9-yl)-2-cyclopentene-1-methanol from Example 4 (0.544 g, 2 mmol), aminomethylcyclopropane hydrochloride (0.323 g, 3 mmol), triethylamine (0.607 g, 6 mmol) and methanol (15 mL) were heated in a Parr bomb for 12 hours. During this time an additional aminomethylcyclopropane hydrochloride (0.108 g, 1 mmol) and triethylamine (0.101 g, 1 mmol), were added. 1 N NaOH (2 ml) was added and solution concentrated under vacuum, dried by evaporation of ethanol, and chromatographed on silica gel. Title compound was eluted in 5% methanolchloroform; white powder after crystallization from acetonitrile (0.425 g, 71%), m.p. 182–183° C.

$^1$H-NMR: (DMSO-$d_6$) δ 7.5 H-8), 6.10 and 5.85 (2 m, overlapping s at 5.77, total 4, CH=CH and NH$_2$), 5.40 (br m, 1, CH—N), 4.73 (t, J=5.3, 1, OH), 3.45 (m, 2, CH$_2$-O), 3.40–3.20 (m, overlapping H$_2$O, CH$_2$-NH), 2.85 (br m, 1, CH), 2.70–2.50 (m, overlapping solvent, 0.5 CH$_2$), 1.70–1.50 (m, 1, 0.5 CH$_2$, 1.20–1 0 (m, 1, CH—CH$_2$NH), 0.45–0.20 (m, 2, CH$_2$—CH$_2$ cyclopropyl.

Anal. Calcd. for C$_{15}$H$_{20}$N$_6$O: C, 59.98; H, 6.71; N, 27.98.

Found: C, 59.90, 59.83; H, 6.72, 6.76; N, 27.91.

EXAMPLE 48

(±)-cis-4-(2-Amino-6-(cyclobutylthio)-9H-purin-9-yl)-2-cyclopentene-1-methanol

A mixture of (±)-cis-2-amino-1,9-dihydro-9-[(4-hydroxymethyl)-2-cyclopenten-1-yl]-6H-purine-6-thione hydrochloride from Example 8 (500 mg, 1.45 mmol), potassium carbonate (600 mg) and cyclobutylbromide (0.98 g, 7.25 mmol), added in 5 portions over 18 hours in dry N,N-dimethylformamide (20 mL) was stirred under nitrogen for 24 hours at 25° C. The N,N-dimethylformamide was removed under reduced pressure. The residual oil was partitioned between chloroform and water. The chloroform layer was dried (MgSO$_4$) and concentrated to a yellow glass which was chromatographed on silica gel. Title compound was eluted with 6% methanol-chloroform and crystallised four times from acetonitrile to give pale yellow granules (0.115 g, 25%) m.p. 159–160° C.

$^1$H-NMR: (DMSO-$d_6$) δ 7.81(s,1,H-8), 6.41 (br s, 2, NH$_2$), 6.10 and 5.85 (2 m, 2, CH=CH), 5.40 (br m, 1, CH—N), 4.69 (1 J=5.3) overlapping 4.70–4.50 (m, total 2, OH and S-CH), 3.45 (m, 1, CH$_2$-O), 2.80 (br m, 1, CH), 2.70–1.90 (m, overlapping solvent, 05. CH$_2$ and 3 cyclobutyl CH$_2$), 1.70–1.50 (m, 1, 0.5 CH$_2$).

Anal. Calcd. for C$_{15}$H$_{19}$N$_5$OS: C, 56.76; H, 6.03; N, 22.06; S, 10.10.

Found: C, 56.75; H, 6.07; N, 21.98; S, 10.04.

EXAMPLE 49

(±)-cis-4-(2-Amino-6-((2.3-dihydroxypropyl)amino)-9H-purin-9-yl)-2-cyclopentene-1-methanol A solution of (±)-cis-4-(2-amino-6-chloro-9H-purin-9-yl)-2-cyclopentene-1-methanol from Example 4 (0.544, 2 mmol), 3-amino-1,2-propanediol (1.87 mg, 2 mmol), triethylamine (607 mg, 6 mmol) and methoxyethanol (6 ml) were refluxed overnight under nitrogen. 1 N NaOH (2 ml) was added and the solution was concentrated under vacuum and dried by evaporation of ethanol. The residual oil was chromatographed on silica gel. Title compound was eluted with 20% methanol-chloroform; white powder after crystallization from acetonitrile-methanol (0.300 g, 47%), m.p. 119–121° C.
$^1$H-NMR: (DMSO-$d_6$) δ 7.60 (s, 1, H-8), 6.90–6.80 (br m, 1, NH), 6.10 (m, 1, =CH), 5.85 (m, 3, =CH and NH$_2$), 5.40 (br m, 1, CH—N), 4.90 (m, 1, OH), 4.72 (t, J=5.3,1, OH), 4.62 (t, J=5.9, 1, OH), CH), 2.70–2.50 (m, overlapping solvent, 0.5 CH$_2$), 1.70–1.50 (m, 1, 0.5 CH$_2$).

Anal. Calcd. C$_{14}$H$_{20}$N$_6$O$_3$0.5H$_2$O: C, 51.06; H, 6.43; N 25.52.

Found: C, 50.99, 50.96; H, 6.45, 6.49; N 25.42, 25.36.

EXAMPLE 50

(±)-cis-4-(2-Amino-6-((2-hydroxy-1-(hydroxymethyl)ethyl)amino)-9H-purin-9-yl)-2-cyclopentene-1-methanol A solution of serinol hydrochloride (0.765 g, 6.00 mmol) in methanol (20 mL) was stirred with basic ion exchange resin for 10 minutes. The resin was filtered off and the filtrate concentrated to a colorless oil. To this was added (±)-cis-4-(2-amino-6-chloro-9H-purin-9-yl)-2-cyclopentene-1-methanol (0.544 g, 2.00 mmol) and methanol (10 mL). The resulting solution was stirred in a Parr bomb at 80° C. overnight. 1N NaOH (2 mL) was added and the solvent evaporated. The residue was chromatrographed on silica gel. Title compound eluted with 20% methanol-chloroform; white powder after crystallization from acetonitrile-methanol (0.404 g, 63%), m.p. 160–162° C.

$^1$H-NMR: (DMSO-$d_6$) δ 7.60 (s, 1, H-8), 6.38 (m, 1, NH), 6.10 (m, 1, =CH), 5.90–5.75 (m, overlapped by s at 5.8; total 3, =CH and NH$_2$), 3.60–3.40 (2 m, 6, 3 CH$_2$-O), 2.75 (br m, 1, CH), 2.70–2.50 (m, 1, 0.5 CH$_2$), 1.65–1.50 (m, 1, 0.5 CH$_2$).

Anal. Calcd. for C$_{14}$H$_{20}$N$_6$O$_3$: C, 52.49; H, 6.29; N, 26.24.

Found: C, 52.38; H, 6.33; N, 26.23.

EXAMPLE 51

(±)-cis-4-(2-Amino-6-pentoxy-9H-purin-9-yl)-2-cyclopentene-1-methanol

To a solution of 1±)-cis-4-(2-amino-6-chloro-9H-purin-9-yl)-2-cyclopentene-1-methanol (0.544 g, 2 mmol) in 1-pentanol (10 mL) at 110° C. was added NaH (60% oil dispersion, 0.160g, 4 mmol). The mixture was stirred at 110° C. for 15 minutes, then cooled to room temperature. 1 N HCl was added to adjust the pH to 7.0, and the solvent was removed by evaporation. The residual oil was chromatographed on silica gel. Title compound was eluted with 7% methanol-chloroform; white powder after crystallization from acetonitrile-methanol (0.481g, 76%); mp=139–141° C.;

$^1$H-NMR (DMSO-$d_6$) δ 7.73 (s, 1, H-6), 6.33 (br s, 2, NH$_2$), 6.10 and 5.85 (2 m, 2, CH=CH), 5.40 (br m, 1, CH—N), 4.70 (t, J=5.1, 1, OH), 4.37 (t, J=6.6, 2, CH$_2$CH$_2$-O), 3.45 (m, 2, CH$_2$-$_0$), 2.85 (br m, 1, CH), 2.70–2.55 (m, 1, ½CH$_2$), 1.70–1.20 (all m, 7, 3 CH$_2$ and ½CH$_2$), 0.90 (m, 3, CH$_3$).

Anal. calcd. for C$_{16}$H$_{23}$N$_5$O$_2$, C, 60.55; H, 7.30; N, 22.07.

Found: C, 60.30; H, 7.35; N, 21.92.

EXAMPLE 52

(±)-cis-4-(2-Amino-6-hexoxy-9H-purin-9-yl)-2-cyclopentene-1-methanol

To a solution of (±)-cis-4-(2-amino-6-chloro-9H-purin-9-yl)-2-cyclopentene-1-methanol (0.549 g, 2 mmol) in 1-hexanol (10 ml) at 110° C. was added NaH (60% oil dispersion, 0.16 g, 4mmol). The mixture was stirred at 110° C. for 20 minutes, then cooled to room temperature. 1 N HCl was added to adjust the pH to 7.0, and the solvent was removed by evaporation. The residual oil was chromatographed on silica gel. The title compound was eluted with 7% methanolchloroform; white powder after crystallization from acetonitrilemethanol (0.397 g, 60%); MP 90–92° C.;

'H-NMR (DMSO-d$_6$) δ: 7.73 (s, 1, H-8), 6.34 (br s, 2, NH$_2$), 6.10 and 5.85 (2 m, 2, CH=CH), 5.40 (br m, 1, CH—N), 4.70 (t, J=5.0, 1, OH), 4.37 (t, J=6.6, 2, CH2CH$_2$O), 3.45 (m, 2, CH$_{2-0}$ $_{2.85}$ (br m, 1, CH), 2.70–2.55 (m, 1, ½CH$_2$), 1.80–1.20 (all m, 8, 4 CH$_2$ and ½CH$_2$), 0.86 (m, 3, CH$_3$).

Anal. Calcd. for C$_{17}$H$_{25}$N$_5$O$_2$ C, 61.61; H, 7.60; N, 21.13.

Found: C, 61.51; H, 7.63; N, 21.06.

EXAMPLE 53

(±)-cis-4-(2-Amino-6-(ethylamino)-9H-purin-9-yl)-2-cyclopentene-1-methanol (±)-cis-4-(2-Amino-6-chloro-9H-purin-9-yl)-2-cyclopentene-1-methanol (0.544g, 2 mmol) was added to an ethyl amine-saturated methanol solution (14 mL). The solution was heated at 80° C. in a Parr bomb for 2.5 hours. 1 N NaOH (2 mL) was added, and solvent evaporated. The residual oil was chromatographed on silica gel. Title compound was eluted with 10% methanol-chloroform; white crystals after crystallization from acetonitrile-methanol (0.365 g, 67%); mp 171–173° C.;

$^1$H-NMR (DMSO-d$_6$) δ 7.57 (s, 1, H-8), 7.10 (br m, 1, NH), 6.10 and 5.85 (2m, 2, CH=CH), 5.76 (br s, 2, NH$_2$), 5.40 (br m, 1, CH—N), 4.73 (t, J=5.1, 1, OH), 3.45 (M, 4, CH$_{2-0}$, CH$_2$-N), 2.85 (br m, 1, CH) 2.65–2.50 (m, overlapping solvent, ½CH$_2$), 1.70–1.50 (m, 1, ½CH$_2$), 1.13 (t, J=7.0, 3, CH$_3$).

Anal. Calcd. for C$_{13}$H$_{18}$N$_6$O: C, 56.92; H, 6.61; N, 30.64.

Found: C, 56.89; M, 6.62; N, 30.71.

EXAMPLE 54

(±)-cis-4-(2-Amino-6-(trans-2-phenylcyclopropylamino)-9H-purin-9-yl)-2-cyclopentene-1-methanol A solution of trans-2-phenyl cyclopropylamine.HCl (1.02 g, 6 mmol) in methanol (10 ml) was stirred with basic ion exchange resin for 5 minutes. The resin was filtered off and the filtrate was concentrated to a colorless oil. To this was added (±)-(cis)-4-(2-amino-6-chloro-9H-purin-9-yl)-2-cyclopentene-1-methanol (0.549 g, 2 mmol). The resulting solution was stirred in a Parr bomb at 80° C. for 12 hours 1 N NaOH 12 ml) was added and the solvent evaporated. The residual oil was chromatographed on silica gel. Title compound was eluted with 5% methanol-chloroform to give tan crystals after crystallization from acetonitrile-methanol (0.221 g, 30%), m.p.=188–190° C.

$^1$H-NMR (DMSO-d$_6$) δ 7.62 (s, 1, H-8), 7.55 (br m, 1, NH), 7.35–7.10 (all m, 5, C$_6$H$_5$), 6.10 and 5.85 (2m, 2, CH=CH), 5.78 (br s, 2, NH$_2$), 5.40 (br m, 1, CH—N), 4.75 (t, J=5.1, 1, OH), 3.45 (m, 2, CH$_2$-O), 3.35–3.25 (m, overlapping H$_{20}$, CH—NH), 2.85 (br m, 1, CH), 2.70–2.55 (m, 1, ½CH$_2$), 2.20–2.10 (m, 1, CH-Ph), 1.65–1.55 (m, 1, ½CH$_2$), 1.40–1.15 (m, 2, CH$_2$ cyclopropyl).

Anal. Calcd. for C$_{20}$H$_{22}$N$_6$O: C, 66.28; H, 6.12; N, 23.19.

Found: C, 66.03; H, 6.19; N, 22.97.

EXAMPLE A

Tablet Formulations

The following formulations A, B and C are prepared by wet granulation of the ingredients with a solution of povidone, followed by addition of magnesium stearate and compression.

|   |   | mg/tablet | mg/tablet |
|---|---|---|---|
|   | Formulation A | | |
| (a) | Active ingredient | 250 | 250 |
| (b) | Lactose B.P. | 210 | 26 |
| (c) | Povidone B.P. | 15 | 9 |
| (d) | Sodium Starch Glycollate | 20 | 12 |
| (e) | Magnesium Stearate | 5 | 3 |
|   |   | 500 | 300 |
|   | Formulation B | | |
| (a) | Active ingredient | 250 | 250 |
| (b) | Lactose | 150 | — |
| (c) | Avicel PH 101 | 60 | 26 |
| (d) | Povidone B.P. | 15 | 9 |
| (e) | Sodium Starch Glycollate | 20 | 12 |
| (f) | Magnesium Stearate | 5 | 3 |
|   |   | 500 | 300 |
|   | Formulation C | | |
|   | Active ingredient | 100 | |
|   | Lactose | 200 | |
|   | Starch | 50 | |
|   | Povidone | 5 | |
|   | Magnesium stearate | 4 | |
|   |   | 359 | |

The following formulations, D and E, are prepared by direct compression of the admixed ingredients. The lactose in formulation E is of the direct compression type (Dairy Crest - "Zeparox").

|   |   | mg/tablet |
|---|---|---|
|   | Formulation D | |
|   | Active ingredient | 250 |
|   | Pregelatinised Starch NF15 | 150 |
|   |   | 400 |
|   | Formulation E | |
|   | Active ingredient | 250 |
|   | Lactose | 150 |
|   | Avicel | 100 |
|   |   | 500 |

Formulation F (Controlled Release Formulation)

The formulation is prepared by wet granulation of the ingredients (below) with a solution of povidone followed by the addition of magnesium stearate and compression.

|   |   | mg/tablet |
|---|---|---|
| (a) | Active ingredient | 500 |
| (b) | Hydroxypropylmethylcellulose (Methocel K4M Premium) | 112 |
| (c) | Lactose B.P. | 53 |
| (d) | Povidone B.P. | 28 |
| (e) | Magnesium Stearate | 7 |
|   |   | 700 |

Drug release takes place over a period of about 6–8 hours and is complete after 12 hours.

EXAMPLE B

Capsule Formulations

Formulation A

A capsule formulation is prepared by admixing the ingredients of Formulation D in Example A above and filling into a two-part hard gelatin capsule. Formulation B (infra) is prepared in a similar manner.

|     |                          | mg/capsule |
|-----|--------------------------|------------|
|     | Formulation B            |            |
| (a) | Active ingredient        | 250        |
| (b) | Lactose B.P.             | 143        |
| (c) | Sodium Starch Glycollate | 25         |
| (d) | Magnesium Stearate       | 2          |
|     |                          | 420        |
|     | Formulation C            |            |
| (a) | Active ingredient        | 250        |
| (b) | Macrogol 4000 B.P.       | 350        |
|     |                          | 600        |

Capsules of formulation C are prepared by melting the Macrogol 4000 BP, dispersing the active ingredient in the melt and filling the melt into a two-part hard gelatin capsule.

| Formulation D     |            |
|-------------------|------------|
|                   | mg/capsule |
| Active ingredient | 250        |
| Lecithin          | 100        |
| Arachis Oil       | 100        |
|                   | 450        |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b and c using an extruder, followed by spheronisation of the extrudate and drying. The dried pellets are then coated with release-controlling membrane (d) and filled into a two-piece, hard gelatin capsule.

|     |                          | mg/capsule |
|-----|--------------------------|------------|
| (a) | Active ingredient        | 250        |
| (b) | Microcrystalline Cellulose | 125      |
| (c) | Lactose B.P.             | 125        |
| (d) | Ethyl Cellulose          | 13         |
|     |                          | 513        |

EXAMPLE C

Injectable Formulation

| Formulation A                        |           |
|--------------------------------------|-----------|
| Active ingredient                    | 0.200 g   |
| Hydrochloric acid solution, 0.1M, or |           |
| Sodium hydroxide solution, 0.1M q.s. to pH | 4.0 to 7.0 |
| Sterile water q.s. to                | 10 ml     |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

| Formulation B                                |          |
|----------------------------------------------|----------|
| Active ingredient                            | 0.125 g  |
| Sterile, pyrogen-free, pH 7 phosphate buffer q.s. to | 25 ml |

EXAMPLE D

| Intramuscular injection    |         |
|----------------------------|---------|
| Active ingredient          | 0.20 g  |
| Benzyl Alcohol             | 0.10 g  |
| Glycofurol 75              | 1.45 g  |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE E

| Syrup                    |           |
|--------------------------|-----------|
| Active ingredient        | 0.25 g    |
| Sorbitol Solution        | 1.50 g    |
| Glycerol                 | 2.00 g    |
| Sodium Benzoate          | 0.005 g   |
| Flavor, Peach 17.42.3169 | 0.0125 ml |
| Purified Water q.s. to   | 5.00 ml   |

The active ingredient is dissolved in a mixture of the glycerol and most of the purified water. An aqueous solution of the sodium benzoate is then added to the solution, followed by addition of the sorbitol solution and finally the flavor. The volume is made up with purified water and mixed well.

EXAMPLE F

| Suppository                         |                |
|-------------------------------------|----------------|
|                                     | mg/suppository |
| Active ingredient (631 m)*          | 250            |
| Hard Fat, BP (Witepsol H15 - Dynamit NoBel) | 1770   |
|                                     | 2020           |

*The active ingredient is used as a powder wherein at least 90% of the particles are of 631 m diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C, the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

EXAMPLE G

| Pessaries | |
|---|---|
| | mg/pessary |
| Active ingredient (631 m)' | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture

Antiviral Activity

The compounds of Examples 14 and 16 were tested for anti-HIV activity in MT$_4$ cells according to the method described by Averett, D. R., *J. Virol Methods.* 1989, 23, 263–276 and were found to have IC$_{50}$ values of 24 μM and 15 μM, respectively.

TOXICITY DATA

Determination of Growth Inhibition of Uninfected Mammalian Cells

The capability of candidate compounds to inhibit the growth of D98 cells (human) and L cells (purine) was measured by determination of cell number following three days exposure of a standard number of cells to various dilutions of compound (Rideout, J. L., Krenitsky, T. A., Koszalka, G. W., Cohn, N. K., Chao, E. Y. Elion, G. B., Latter, V. S., and Williams, R. B. (1982) *J. Med Chem.* 25: 1040–1044). The cell number was then compared to the number obtained in the absence of compound. Cell enumeration was performed by either direct particle counts following trypsinization of the monolayer, or by spectrophotometric determination of the amount of vital stain taken up by the cells. Comparable results were obtained with both methods.

Data Analysis

The concentration of compound resulting in 50% of control values (IC$_{50}$) was calculated either by direct interpolation from graphs of the log of the compound concentration versus the percent of control value, or from a computer program which analyses the data according to the same algorithm. Data in the range of 20% to 80% of control were used in these calculations. All compounds were tested in D-98 cells and found to have an IC$_{50}$ value of >100 μm.

I claim:

1. A compound (±)-cis-4-(2-amino-6-(allylthio)-9H-purin-9-yl)-2-cyclopentene-1-methanol.
2. A compound (±)-cis-4-(2-amino-6-cyclopentyloxy-9H-purin-9-yl)-2-cyclopentene-1-methanol.
3. A compound (±)-cis-4-(2-amino-6-(Allylamino)-9H-purin-9-yl)-2-cyclopentene-1-methanol.
4. A compound (±)-cis-4-(2-amino-6-(cyclopentylthio)-9H-purin-9-yl)-2-cyclopentene-1-methanol.
5. A compound (±)-cis-4-(2-amino-6-(cyclopbutylthio)-9H-purin-9-yl)-2-cyclopentene-1-methanol.

* * * * *